US010004859B2

(12) United States Patent
Winkler et al.

(10) Patent No.: US 10,004,859 B2
(45) Date of Patent: Jun. 26, 2018

(54) ATOMIZER

(71) Applicant: Boehringer Ingelheim International GmbH, Ingelheim am Rhein (DE)

(72) Inventors: Robert Gerhard Winkler, Aschaffenburg (DE); Herbert Wachtel, Ingelheim am Rhein (DE); Stephen Terence Dunne, Ipswich (GB); Andree Jung, Idar-Oberstein (DE)

(73) Assignee: Boehringer Ingelheim International GmbH, Ingelheim am Rhein ( * ) Notice: Subject to any disclaimer, the term of this patent is extended or adjusted under 35 U.S.C. 154(b) by 644 days.

(21) Appl. No.: 14/399,740

(22) PCT Filed: Apr. 30, 2013

(86) PCT No.: PCT/EP2013/059011

§ 371 (c)(1),
(2) Date: Nov. 7, 2014

(87) PCT Pub. No.: WO2013/167429

PCT Pub. Date: Nov. 14, 2013

(65) Prior Publication Data

US 2015/0122257 A1 May 7, 2015

(30) Foreign Application Priority Data

May 9, 2012 (EP) .................................... 12167219
Oct. 29, 2012 (EP) .................................... 12190436

(51) Int. Cl.

| | |
|---|---|
| ***A61M 11/00*** | (2006.01) |
| ***A61M 15/00*** | (2006.01) |
| ***A61M 11/02*** | (2006.01) |
| ***A61M 11/04*** | (2006.01) |
| ***A61M 16/10*** | (2006.01) |
| *A61M 16/00* | (2006.01) |

(52) U.S. Cl.
CPC ........ *A61M 15/009* (2013.01); *A61M 11/002* (2014.02); *A61M 11/02* (2013.01);
(Continued)

(58) Field of Classification Search
CPC .. A61M 11/00; A61M 11/002; A61M 11/006; A61M 11/02; A61M 11/041;
(Continued)

(56) References Cited

U.S. PATENT DOCUMENTS 4,171,000 A 10/1979 Uhle
7,455,248 B2 * 11/2008 Kablik .................. A61K 31/74 239/362
(Continued)

FOREIGN PATENT DOCUMENTS

EP 0820780 A1 1/1998
EP 1731186 A1 12/2006
(Continued)

OTHER PUBLICATIONS

International Search Report for PCT/EP2013/059011 dated Jun. 19, 2013.

*Primary Examiner* — Lynne Anderson
(74) *Attorney, Agent, or Firm* — Marc Began; Philip I. Datlow

(57) ABSTRACT

The invention relates to an apparatus for nebulizing preferably powdered medicinal formulations, the nebulization being assisted by propellant. According to the invention, the propellant is supplied in pulsed form to the powder cavity (1) containing the formulation, which is attached to the nozzle (3) from which the aerosol is emitted. The apparatus according to the invention provides an increase in the fraction of pulmonary particles in the aerosol leaving the nozzle (3).

23 Claims, 12 Drawing Sheets

(52) U.S. Cl.
CPC ........ *A61M 11/041* (2013.01); *A61M 15/002* (2014.02); *A61M 15/0021* (2014.02); *A61M 15/0025* (2014.02); *A61M 15/0035* (2014.02); *A61M 15/0043* (2014.02); *A61M 15/0045* (2013.01); *A61M 15/0051* (2014.02); *A61M 15/0055* (2014.02); *A61M 15/0086* (2013.01); *A61M 16/109* (2014.02); *A61M 2016/0015* (2013.01); *A61M 2016/0039* (2013.01); *A61M 2202/064* (2013.01); *A61M 2205/8225* (2013.01)

(58) Field of Classification Search
CPC .......................... A61M 11/042; A61M 11/044; A61M 15/002; A61M 15/0021; A61M 15/086; A61M 15/09; A61M 15/0045; A61M 15/0046; A61M 15/0051; A61M 2205/8225; A61M 15/009
See application file for complete search history.

(56) References Cited

U.S. PATENT DOCUMENTS

| | | | | |
|---|---|---|---|---|
| 7,464,704 | B2 * | 12/2008 | Braithwaite .......... | A61M 15/00 128/200.12 |
| 7,533,668 | B1 | 5/2009 | Widerstrom | |
| 8,776,786 | B2 * | 7/2014 | Kraft ...................... | A61M 11/06 128/200.22 |
| 9,269,974 | B2 | 2/2016 | Matsusue | |
| 2002/0088462 | A1 | 7/2002 | Genova | |
| 2005/0121025 | A1 | 6/2005 | Gamard | |
| 2005/0126562 | A1 * | 6/2005 | Rabinowitz ........... | A61M 15/00 128/200.23 |
| 2005/0207984 | A1 | 9/2005 | Oliver | |
| 2009/0293873 | A1 | 12/2009 | Djupesland | |
| 2011/0297151 | A1 | 12/2011 | Jung | |

FOREIGN PATENT DOCUMENTS

| | | | |
|---|---|---|---|
| EP | 2042208 | A1 | 4/2009 |
| GB | 1562098 | A | 3/1980 |
| JP | 62249656 | A | 10/1987 |
| WO | 8704354 | A1 | 7/1987 |
| WO | 02056948 | A1 | 7/2002 |
| WO | 03045483 | A2 | 6/2003 |
| WO | 2003045483 | A2 | 6/2003 |
| WO | 2004110536 | A1 | 12/2004 |
| WO | 2006090149 | A2 | 8/2006 |
| WO | 2009040044 | A2 | 4/2009 |
| WO | 2011067763 | A1 | 6/2011 |
| WO | 2011077414 | A2 | 6/2011 |

* cited by examiner

ATOMIZER

FIELD OF THE INVENTION

The present invention relates to apparatus for nebulising medicinal formulations, wherein the nebulisation of the formulation is assisted by propellants. In particular, the invention relates to apparatus that can be used as an inhaler for administering powdered formulations.

BACKGROUND OF THE INVENTION

The use of medicaments that are administered using inhalers is targeted particularly on interactions with particular regions of the respiratory system of a patient. These regions comprise the nasal passages, the pharynx and various places within the lungs, such as the bronchi, bronchioles and alveoli. The possibility of administering medicaments to one of these target regions is dependent inter alia on the aerodynamic diameters of the respective particles or droplets which are breathed in when the inhaler is used. The current assumption is that particles with aerodynamic diameters of between 2 and about 5 microns can be supplied satisfactorily to the bronchi and bronchioles. Smaller particles may potentially penetrate into the alveoli. Particles with an aerodynamic diameter of more than 6 microns and especially more than 10 microns are typically suitable for deposition in the pharynx and nasal passages.

In the case of inhalers which are intended to deliver a medicament into the lung, it is generally desirable if a large proportion of the medicament administered, particularly with respect to the particle size, is inhalable and it is possible to achieve a high deposition rate of the medicament in the lung itself. This depends on a number of factors such as, in particular, the properties of a spray mist produced with the inhaler. These properties are, for example, the speed of the mist, the size of the particles and their size distribution, the proportion of small particles, the constituents of the gas, etc.

The following description will concentrate on the administration of powdered formulations, but is also applicable to the administration of liquid formulations.

Many powder inhalers are already on sale or are otherwise known. A distinction is made between two types of inhalers: active and passive. In passive inhalers, the inward breath of the user or patient alone is used to break up the powder and carry the powder into the lungs. The carrying and breaking up of the powder are therefore dependent on the flow rate at which the patient breathes air in through the apparatus. As a result, the inhalable content or the part of the powder that actually reaches the lungs is highly dependent on the breathing behaviour of the patient and varies from one patient to the next. Active inhalers, unlike passive inhalers, contain an additional energy source which assists with the break-up and conveying of the powder. The powder is actively nebulised with apparatus of this kind.

Active inhalers, with their high market share over many years, are in particular conventional propellant-driven metering aerosols (hereinafter frequently referred to by the conventional English abbreviation MDI, standing for "metered dose inhaler"). In an MDI the medicament is present as a suspension or solution in a propellant. The propellant is contained under excess pressure in a container with a metering valve. On activation, the metering valve delivers a single measured amount (dose) of the medicament in the form of a gas stream. Propellants suitable for MDIs may contain hydrofluoroalkanes (HFA) or other fluorohydrocarbons (FHC) with low boiling points. Because of the high pressure difference between the inside of the propellant container (typically around 5 bar) and the ambient air (1 bar), in conventional MDIs the propellant is expelled at a high speed which may even enter the supersonic speed range. As a result, the time for emptying the valve chamber and hence the duration of a nebulisation is so short (typically about 50 milliseconds when delivering 100 microliters) that it is difficult for a patient to adapt their breathing to the short pulse such that they are actually able to breathe in the entire volume nebulised. Moreover, the propellant is partially expelled from the apparatus in liquid form. As a result, and because of the high exit speed, a large proportion of the medicament is delivered in such a coarse form that it is deposited directly in the patients' oropharyngeal cavity without being able to be carried into the lungs.

WO2004110536A1 shows a delivery device for a powdered medicament in which a receptacle containing powdered medicament and a propellant source are arranged in a housing such that the propellant strikes the powdered medicament through an inlet. In the receptacle, the aerosol thus formed is able to expand before being expelled from the device through an exit opening. For the device, replacement inserts are provided with combined powder and propellant inserts. Possible propellant sources specified are compressed gases such as carbon dioxide, nitrogen or air, or fluorohydrocarbons such as HFA-134a or HFC-227 are mentioned as conventional propellants. Within the scope of tests for clinical trials, the specification WO2004110536A1 mentions, inter alia, nebulisation results for device configurations having receptacles filled with 120 milligrams of micronized active substance and nitrogen as propellant at pressures of 6 to 14 bar. In comparison to the test data described, standard commercial (not capsule-based, usually passive) powder inhalers as a rule deliver powder units of the order of 6 to 400 micrograms in size per application (when capsules are used, larger amounts of filling are known; thus, a capsule-based powder inhaler is also known in which the capsule holds 28 milligrams). The widely used MDIs based on delivery using propellants typically deliver only about 200 micrograms of active substance per application. Inhalers for delivering larger amounts of formulation are not available on the market in this context, as far as the inventors are aware.

The specification U.S. Pat. No. 4,534,345 shows, for example, an active inhaler which contains a propellant container, a storage chamber with pharmaceutically active substance in solid, micronized form and a dose charging device with a perforated membrane. In a first position, perforations in the membrane are filled with the substance, in a second the perforations are pushed into a channel for the propellant. When an associated device is actuated, the propellant is released from its container into the channel and expels the substance through a nozzle of the inhaler.

Inhalers for dry powder are divided into devices for administering individual dosage units and into multi-dose devices. Multi-dose devices are also subdivided into devices with pre-metered and individually stored dosage units (the usual abbreviation "pmDPI" is used, from the corresponding English term "pre-metered Dry Powder Inhaler" and devices in which each powder unit is measured out from a reservoir inside the device by means of a measuring device.

The use of pmDPIs has the advantage that the individual dosage units are measured out under controlled factory conditions and the powder can be protected comparatively easily from the ambient air and other external influences. In many applications a formulation is used in the form of a mixture of an active substance and a carrier substance such as lactose. The lactose and/or the active substance or active substances tend to absorb moisture from the ambient air, thus resulting in clumping of the powder and difficulties in breaking it up or nebulising it and in delivering the powder into the lungs.

The specification DE4106379A1 shows a passive inhaler in which the powder is contained in pre-metered inhalable amounts in pouches of a flexible strip-like carrier. This carrier consists of a carrier web forming the pouches and a cover strip that closes off the pouches. The inhaler comprises, in addition to a receptacle for the powder carrier, an opening station with a pulling device which pulls the cover strip and the carrier web apart in order to open the pouches. Powder can be aspirated from the opened pouch through a powder outlet.

The specification EP1992381A1 discloses an active pmDPI with an annular storage device that can be rotated step by step, with a plurality of inserts, each insert containing a single dose of a medicinal formulation in a storage chamber and a nozzle. The inserts are contained in separate, sealed cavities which are opened individually to deliver the individual dose. To expel the dose, the respective insert is connect by means of a connecting element to an air pump with bellows.

A similar active pmDPI is disclosed in the specification WO2009040044. This additionally shows that the connecting element between the pump and the insert constitutes a construction which, together with the air pump, forms a resonance system. This resonance system operates such that the build-up of pressure of the compressed air produced by the air pump does not rise in a strictly uniform manner during the delivery of the dose but is modulated in pulsed manner.

The specification WO2009083244A2 shows an active pmDPI in which the individual doses of the medicinal formulation are contained in storage units in an oblong carrier. Apart from a storage chamber with formulation each storage unit comprises a nozzle for individually releasing the respective dose. In one embodiment, the nozzles are exposed one after another by the removal of a cover strip. To expel the formulation from the individual storage units the associated storage chamber is also pierced with a piercing element, allowing pressurised gas to enter the storage chamber, thereby carrying the formulation with it. The pressurised gas is provided by an air pump or alternatively from a container holding liquefied gas. In one embodiment, the delivery of the respective dose by compressed air is triggered by detection of an inward breath.

The specification GB2233236A shows an MDI with so-called breath actuation. In this device, a measured dose is conveyed from a pressurised container, with medicament suspended or dissolved in liquid propellant, into a storage chamber in which a valve in a closed position closes off the outlet. The valve, e.g. a magnetic plate valve or a piston valve provided with a restoring spring, is part of a delivery device controlled by the patient's inhalation.

The problem which the present invention addresses is to provide a device which is an improvement on the prior art, for nebulising preferably powdered medicinal formulations for inhalation. In particular a device is to be provided in which comparatively large measured amounts of substance, particularly greater than 1 milligram of active substance, can be expelled for inhalation or with which large inhalable dosage amounts of the medicinal formulation can be prepared. Particularly preferably, in the embodiment of the device as an inhaler, the pulmonary fraction of a quantity of formulation delivered in aerosol form with this device should be only slightly, or not at all, dependent on the breathing characteristics of the user, i.e. the patient. Moreover, the device should be configured advantageously, particularly in terms of the aspect of error-free use by a user, particularly with regard to the coordination of the breathing characteristics with the nebulisation.

SUMMARY OF THE INVENTION

The problem stated above is solved according to the invention by a device for nebulising medicinal formulations, wherein, in the device, the nebulisation is assisted by a propellant which is supplied to a cavity in which is located a measured amount of the formulation, the propellant being supplied to the cavity in the form of a plurality of successive pulses or bursts which are kept distinct from one another.

The present invention relates to the nebulisation of medicinal formulations. By the term "medicinal formulation" or "medicament formulation" are meant, in the present invention, besides medicaments, also therapeutic agents or the like, thus in particular all kinds of agent for inhalation or other forms of administration. The term "formulation" here relates particularly to powders but may also include liquids. Accordingly, the particles may be both solid and liquid. The term "liquid" includes, besides pure liquids and solutions, dispersions, suspensions, suslutions (mixtures of solutions and suspensions) or the like.

In particular, the present invention relates to inhalers for delivering dry powder into the lungs.

The device of the present invention delivers a spray mist which preferably has a high proportion of particles with diameters of 6 microns or less, preferably less than 5 microns.

The present invention relates in particular to a so-called active multi-dose device for delivering an active substance or a formulation for inhalation containing an active substance.

In particular, the invention relates to pmDPIs in which pressurised gas, preferably in the form of compressed air, and/or propellant, preferably an HFA gas such as type R134a, are used in the nebulisation of the powder.

In particular, the device comprises in the region of the propellant feed a device having propellant at its inlet and through which the propellant is passed, the device causing such flow characteristics in the propellant that it exits the device in the form of a plurality of successive pulses or bursts. Preferably, these pulses are kept distinct from one another such that the flow of propellant stalls or comes to a standstill between the pulses (i.e. the pressure of the propellant leaving the device falls to virtually zero, but in any case to a minimal residual flow which may be unavoidable, depending on the technical configuration).

Advantageous further features are described hereinafter and in detail by means of the Figures.

One feature of the present invention is that the propellant is supplied through a valve which divides the propellant present into a plurality of pulses by a number of opening and closing processes. Preferably, liquefied propellant gas is used as the propellant. In particular, the propellant is supplied to the pulse-generating valve from a cartridge in which it is present in liquefied form through a metering valve belonging to the cartridge. (Alternatively, a constant stream of propellant gas, i.e. gaseous propellant, may be present at the pulse-generating valve.) By dividing the burst of propellant from the metering valve into a sequence of a number of short propellant pulses occurring one after another, the delivery time for the medicinal, preferably powdered formulation from the nebuliser is increased. By prolonging the delivery time, a user can adapt his breathing more easily to the aerosol production or coordinate with it than when the aerosol is produced by means of a single burst of propellant as in a conventional MDI, for example. The aerosol production as a whole is extended in time by the pulsing of the propellant.

It has also been found that the pulsing of the propellant with a stopping of the flow of propellant between the pulses has an advantageous effect on the expulsion of powdered formulations from powder cavities in the nebuliser: By expelling the powder using a plurality of bursts or pulses of propellant better emptying of the powder cavities is achieved. This effect is particularly striking when delivering large amounts of powder such as, for example, 20 milligrams or more.

Preferably, the valve is controllable, in that the opening and closing times can be predetermined. An actuatable magnetic valve is highly suitable, for example. In particular, opening times in the range from 3 to 30, particularly preferably in the range from 5 to 10 milliseconds and closure times in the range from 50 to 500 milliseconds, particularly preferably in the range from 100 to 200 milliseconds are set at the valve during operation of the device. It has been found that, in devices for nebulising powdered formulations, the propellant pulses generated by valve opening times of 5 to 10 milliseconds with intermediate closure times of at least 50, preferably at least 100 milliseconds, result in efficient emptying of the powder cavities that hold the formulation. This effect of improved emptying by pulsing of the propellant is all the more marked, the larger the powder cavity. With a pulsed supply of propellant it is thus possible to deliver large amounts of powder in only one application of the device (for example, tests were successfully carried out with 50 and 75 milligram, but amounts of up to 100 milligram or more are also possible). To summarise, the emptying of the powder cavity is improved by a suitable choice of length and time interval between the pulses of propellant, and nebulisation of comparatively large amounts of powder in only one application of the nebuliser is made possible.

In particular, as an alternative to the incorporation of an actuatable valve in the device according to the invention, a further feature of the present invention is that the pulsing of the propellant is produced by a means for generating oscillations in fluids, particularly by a microfluidic oscillator. The term “fluid” relates here both to liquids and to gases, and in the present invention it relates particularly to the special case of the fluid being a liquefied gas. The microfluidic oscillator is a microfluidic channel structure with at least one fork. Depending on the design of the oscillator the oscillation may be caused for example either by at least one controlled feed in the region of the fork, so that the fluid is passed alternately into one or other channel starting at the fork, or the oscillation may be formed by the collision of two flows from channels adjoining the fork, in a suitable mixing region or in an oscillation chamber. In both cases the so-called Coanda effect is used: a fluid stream leaving a channel and entering an expansion region clings to the wall which is less inclined relative to the axis of the stream. This is the stable orientation of the stream with the Coanda effect. However, if the geometry of the device in question or the corresponding channel structure (based on a fork adjoining a widened region, for example) is symmetrical, the stream may cling to one or other wall and remains in this orientation until other factors such as variations in pressure, turbulence or cross-flows give rise to a change in orientation leading to clinging to the other wall.

Particularly when using liquid gas as propellant, it is also possible to make use of the effect that the liquid is already partly changing into the gaseous phase as it flows through the channel structure as a result of its low boiling point. Thus, as a resulting of the superheating caused, gas bubbles are constantly formed, particularly at places such as, for example, in oscillation chambers or mixing regions, where in the event of turbulence, differences in density in the fluid are produced and hence places with different evaporation characteristics. Gas bubbles of this kind then in turn lead to an expulsion of the propellant in pulses or bursts from an outlet of a mixing region of this kind.

The use of a microfluidic oscillator of this kind in a propellant-driven device for nebulisation has the advantage that because of the small size of a microfluidic oscillator the size of the device for nebulising the medicinal formulation only has to be enlarged a comparatively small amount. In this way a device for pulsing the propellant can be installed in hand-held-devices which can be actuated for use without any external means.

A further feature of the present invention is that the propellant for delivering the medicinal, preferably powdered formulation from a cavity before being supplied to this cavity is passed through a vaporiser or heat exchanger. The vaporiser, preferably made of metal, comprises a cavity with an inlet and an outlet for the propellant. The inlet of the vaporiser is preferably formed in one piece with a component which forms the connection for a valve or oscillator used for generating pulses.

The vaporiser has the effect that the propellant which is present in liquid form in a supply cartridge, for example, is all or virtually all converted into a gaseous state before it is supplied to the cavity with the formulation. The propellant which is held under pressure in liquid form in a conventional cartridge evaporates under normal pressure as a rule at negative temperatures on the Celsius temperature scale. When introduced into the cavity of the vaporiser, it is able to expand there and changes from the liquid to the gaseous state. Particularly if powdered formulations are used, this prevents liquid propellant from causing the powder to clump together and thereby adversely affect the nebulisation of the powder. Thus, by using the vaporiser, the pulmonary content of the aerosol particles produced by the expulsion of propellant is increased.

A further feature of the present invention is that the vaporiser contains heat exchange elements inside it. The heat exchange elements assist or accelerate the evaporation of the liquid propellant in the vaporiser, by giving off heat to the propellant flowing along them. These heat exchange elements are preferably made of metal and have a relatively large surface area, which also promotes the evaporation effect. Preferably, the heat exchange elements are in the shape of spheres and/or wires for this purpose.

A further feature of the present invention is that inside the vaporiser the components of the vaporiser are configured so as to present the least possible flow resistance to the propellant flowing through the vaporiser. In this way, virtually all the speed of flow of the propellant gas can be utilised for the powder nebulisation. Factors that contribute to the reduction in the flow resistance are:

the rotational symmetrical configuration of the vaporiser, conical transitions in the inlet and outlet region of the cavity of the vaporiser, the spherical structure of the heat exchange elements in the vaporiser and/or dimensions of the heat exchange elements such that they do not cause the inlet or outlet of the vaporiser to be moved and such that satisfactory flow is possible through their interstitial spaces.

A further feature of the present invention is that the feeding of propellant into the cavity containing the formulation and the axis of a preferably rectilinear nozzle channel occur at the same point, preferably in the centre, and at the same angle relative to the bottom of the cavity. In this arrangement, the axis of the nozzle channel through which the formulation is expelled by means of propellant from the nozzle of the device or the nebuliser, in the very direction in which the stream of propellant from the powder cavity is largely reflected. In this way, the stream of propellant loaded with formulation does not unnecessarily strike the walls of the cavity on its way out. The cavity is emptied better, or there are no or hardly any deposits of formulation adjacent to the inlet of the nozzle channel. An angle of 45° is advantageous for the construction of a compact nebuliser, for example when a plurality of cavities are successively brought into position for delivering the formulation along a circular radius. However, even rather smaller angles of for example 30° may be advantageous, particularly with elongated cavities, as more formulation then has to be penetrated, so to speak, by the propellant before the propellant stream is reflected. This angle of reflection should be adapted to the optimum configuration of cavity and optionally to an exchange mechanism for cavities filled with formulation.

A further feature of the invention is that the powder cavity is of a streamlined construction. Preferably, it is teardrop-shaped (resembling a teardrop cut lengthways) and/or comprises a well with a teardrop-shaped opening. The powder cavity is preferably arranged in the nebuliser in such a way that the supply of propellant or an air inlet is located in the vicinity of the broad belly of the teardrop shape or at the lower edge of the belly, viewed in the direction of flow, and the narrower part of the teardrop shape converges on the nozzle channel or the narrowing end of the teardrop shape opens directly into the nozzle channel. Particularly preferably, the bottom of the well has a slope which directs the flow entering the powder cavity directly towards the nozzle channel. Such a configuration of the powder cavity leads to virtually total emptying when used. As a result the nebuliser may also be used with lower fill volumes, in relation to the medicinal formulation used, compared with the use of other powder cavities with smaller fill volumes. A further feature of the present invention is that, when embodied as an inhaler, the device is used for delivering a plurality of individually measured amounts of the formulation. For this purpose, the individual amounts of formulation, e.g. individual powder units, are preferably contained in the cavities of a blister strip. The cavities are then successively brought into a removal position in the stream of propellant gas, e.g. by advancing the blister strip. They have previously been opened, for example, by means of a mechanism by which the cavity is pierced, or by which, preferably, a cover film that closes off the cavity is pulled off. The provision of the cavities along a blister strip has the advantage that by rolling or winding up the strip a number of cavities can be provided in a small space. Particularly preferably, the transporting of the blister strip inside the device is controlled by an action on the outside of the device, such as, in particular, the opening or closing of a cover for the mouthpiece.

According to a further feature of the present invention, the delivery of the formulation from the cavity is carried out through a nozzle, the outlet opening of which opens into a mouthpiece which is extended in the direction of flow. Preferably, the protruding section of the mouthpiece, compared with the nozzle outlet, is longer than the nozzle channel in the nozzle. Preferably, the mouthpiece projects 40 to 120 millimeters, particularly preferably 40 to 70 millimeters, beyond the end of the nozzle. With a protruding section of this size, on the one hand the proportion of the pulmonary fine particle content of the aerosol produced is increased compared with devices with shorter protruding sections, and on the other hand the protruding section is not so great that there is an excessive formation of deposits on the inside of the mouthpiece. With larger protruding ranges, particularly for protruding sections of 70 to 120 millimeters, the proportion of the inhalable dose increases further; all that may be required is regular cleaning of the mouthpiece.

To create aerodynamics in the mouth tube which are favourable to the inhalation of the aerosol formed, the mouthpiece further comprises, at the device end (i.e. at the end furthest from the point where a user would place his lips, in the case of a device for inhalation), at least one, preferably 1 to 4, inlet openings. Preferably, the inlet opening on the mouthpiece is configured so that a bypass air flow is formed near the outlet of the nozzle, which particularly preferably surrounds the stream of propellant charged with formulation exiting the nozzle. It is found that the aerodynamics are also favourably influenced if the internal diameter of the mouthpiece at the site of the nozzle outlet is significantly larger, particularly five times larger, than the diameter of the opening of the nozzle outlet.

According to a further feature of the present invention, if embodied as an inhaler, the device has breath actuation which initiates the supply of propellant into the vaporiser. Preferably, a switching element of the breath activation, e.g. in the form of a flow sensor, is located in the region of the inlet openings of the mouthpiece and/or in a channel connected to the inlet openings.

The individual features of the present invention may be used independently of one another or combined with one another.

BRIEF DESCRIPTION OF THE DRAWINGS

Further advantages, features, properties and aspects of the present invention will become apparent from the claims and the following description of preferred embodiments with reference to the drawings, wherein:

FIG. 7 shows various powder cavities for use with a nebuliser according to FIG. 1 and FIG. 2:

FIG. 8 shows an inhaler according to the invention as a hand-held device, while

In the Figures, the same reference numerals have been used for identical or similar parts with which corresponding or comparable properties and advantages are achieved, even if the description has not been repeated.

DETAILED DESCRIPTION OF THE INVENTION

Figure 1:
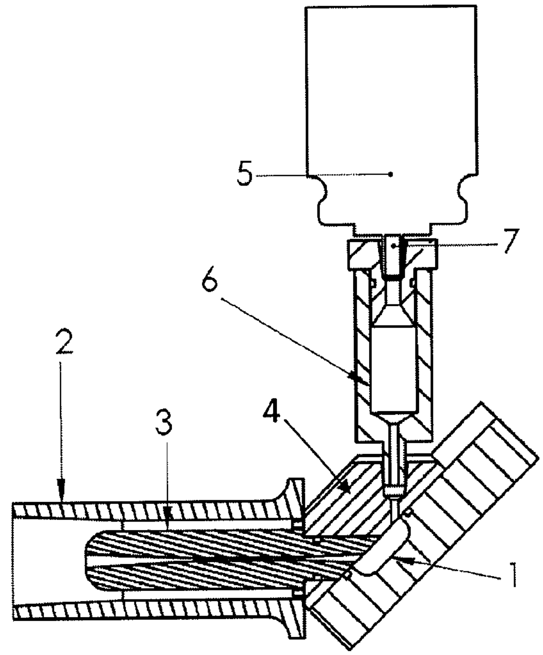
FIG. 1 shows a schematic section through the nebulisation unit of a nebuliser with a propellant feed.

FIG. 1 shows in schematic cross-sectional view the mode of operation of a device which is suitable particularly for the nebulisation of powders. The construction of the device or nebuliser shown is suitable both for an inhaler and also primarily for a test device for checking the operation of individual, replaceably held, components of the inhaler. A nebuliser of this kind embodied as a test device is shown in FIG. 2.

In the nebulisation of powders, propellant is conveyed from a cartridge (5), directly or preferably after passing completely through a vaporiser (6) or heat exchanger, into a powder cavity (1) on which is placed a nozzle (3) which in turn opens into a mouthpiece (2). In the use of a vaporiser (6), as is preferred here, this should be installed in the system so that it is not possible for any of the propellant expelled from the valve on the cartridge (5) to get past the vaporiser (6) via a bypass and enter the powder cavity (1). The propellant expels the powder from the powder cavity (1) through the nozzle (3). If at the same time a user or patient breathes air in through the mouthpiece (2), the powder is picked up by the breathed in air as it leaves the nozzle (2) and flows past the nozzle through the mouthpiece (2) into the lungs. Thus, the powder is carried into the patient's lungs as a result of the suction of his breath.

Both the test device and an inhaler constructed for the same mode of operation are preferably operated by pointing the base of the cartridge (1) upwards, i.e. so that the valve stem (7) of the cartridge (1) is directed downwards. This type of operation is analogous to the operation of a conventional metered dose aerosol (hereinafter frequently referred to by the common English abbreviation MDI). The propellant is metered by means of a valve belonging to the cartridge (again, analogously to the conventional MDI), the release of a unit of propellant being triggered for example by pressure on the base of the cartridge (5).

Figure 2:
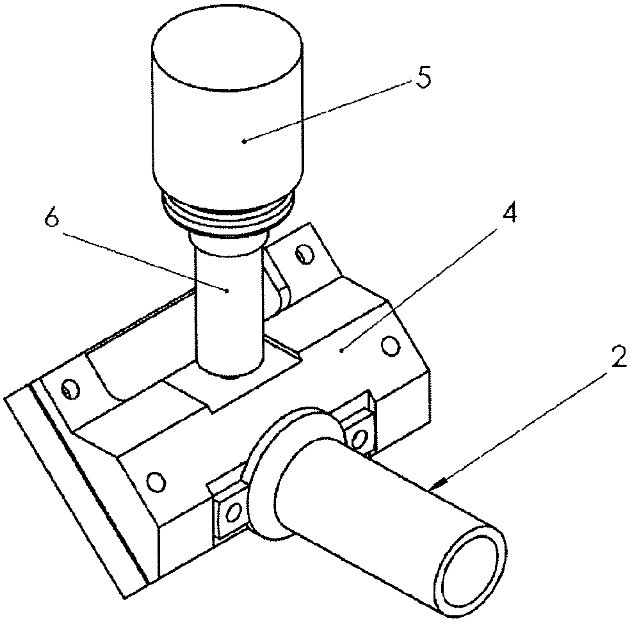
FIG. 2 shows a nebuliser with propellant feed embodied as a test device.

In the test device shown in FIG. 2 the nebuliser consists of individual modules. The functional modules are, in particular, the cartridge (5), the vaporiser (6), the nozzle (3), the mouthpiece (2) and a module that forms the powder cavity (1). Additionally, in the case of the test device, there may also be a connector (4), to which other modules, particularly the nozzle (3), the powder cavity (1) and the vaporiser (6) or the cartridge (5), can be replaceably attached and brought into fluidic relationship with one another.

The test device has the advantage that the modules inserted in the test device can be varied and the effect of the particular variation on the nebulisation characteristics can be determined. Preferably, a system for generating a flow, e.g. a conventional laboratory control panel with a conventional pump, is also connected to the test device so that different suction strengths can be tried out on the mouthpiece (2). The nebulisation of the powder used in the test device can be investigated by the same methods as nebulisation from inhalers, particularly by means of laser diffraction methods, high speed cameras and cascade impactors. The measured results on which this specification is based were determined using a cascade impactor configured as stipulated in the European Pharmacopoeia (Version 7.0) ("Apparatus E" according to Chapter 2.9.18 of the European Pharmacopoeia) to determine the fine particle content of the delivered dose (the measurements additionally being carried out at different flow rates). This fine particle content relates to particle sizes less than 5 microns in diameter and is occasionally also referred to by the abbreviation FPD (derived from the frequently used English term "Fine Particle Dose"). In the measurements with the cascade impactor used for this purpose, the deposits of active substance on the individual collection plates forming the cascade stages and the connection of the cascade impactor were individually washed for each measurement and the resulting solutions were investigated by high pressure liquid chromatography. Different size categories of nebulised particles are collected in the individual cascade stages during measurement, so that the respective amounts of the dose for each size category can be determined by chromatography of the solution from the respective cascade stage. The test device is preferably used for testing the nebulisation of powdered medicinal formulations. Preferred formulations consist of jet-ground and screened active substance which is mixed with lactose. Any desired mixing ratios up to pure active substance can be tested using the test device.

For most measurements a powder cavity (1) with a capacity of about 0.2 milliliters was used, into which usually 50 milligrams of a lactose-based formulation containing 32.5% of an active pharmaceutical substance (an active substance in development) were placed. For the nebulisation concept described here, however, powder cavities (1) may also be filled with amounts of up to 100 milligrams of powder; 21 milligrams, 60 milligrams, 70 milligrams and 75 milligrams were tested, for example (some of them with a formulation containing 98% fenoterol-HBr, as this active substance is well suited to the extreme testing of the nebulisation of inhalers). The size of the powder cavity (1) may be adapted to the amount of powder to be contained therein. Amounts of up to 250 milligrams of powder are possible if the powder cavity (1) and the propellant feed are suitably adapted (up to higher pressures and greater bursts of propellant). The shape of the powder cavity is preferably adapted to the design of the nozzle attached thereto. The expulsion of such large amounts of powder, compared with standard commercial powder inhalers, is made possible in this case by the use of propellants. Preferably, hydrofluoroalkanes (so-called HFAs) are used. Particularly preferably, HFA R134a (norflurane or 1,1,1-trifluoroethane or 1,1,1,2-tetrafluoroethane) is used as propellant in the cartridge (1); preferably, cartridges with metering valves which expel 100 microliters per activation are used. The size of the valve may be adjusted in accordance with the quantity of formulation used; standard commercial sizes such as 25, 50, 100, 180 up to 500 microliters may be used. Thus, within the scope of the results provided here, for smaller amounts of formulation, smaller propellant units were also used, such as for example 50 microliters of propellant to 21 milligrams of powder. Preferably, the standard commercial valves were connected to metallic containers, in particular the valves were crimped to aluminium containers with a capacity of 10 milliliters during the manufacture of the cartridge. The cartridges were filled with the propellant gas R134a. In the cartridge (5) the propellant is present in liquefied form—as in standard commercial metered dose aerosols (MDIs). It evaporates under normal pressure at −26.3° C. and develops a vapour pressure of 5.7 bar at 20° C. However, other propellants such as other hydrofluoralkanes such as, for example, HFA 227ea (apafluran or 1,1,1,2,3,3,3-heptafluoropropane), liquid nitrogen or conventional propellants such as halohydrocarbons may be used in this arrangement.

The test device shown in FIG. 2 is used with the cartridge (5) aligned vertically upwards with the valve stem (7) directed downwards. If, for example, propellant is released by pressing on the upwardly directed base of the cartridge, the propellant flows first into the vaporiser (6) and from there, as a propellant gas, through a line in the connector (4) into the powder cavity (1). The propellant gas then drives the powder in the powder cavity (1) out through the nozzle (3). By using the propellant HFA R 134A with a pressure of about 6 bar at ambient temperature, advantageously higher flow speeds are achieved in the system than with conventional fluorohydrocarbons which when dispensed have pressures only in the range from 2 to 4 bar.

The vaporiser (6) has the effect that the measured amount of propellant released by the metering valve which was present in liquid form in the cartridge (5) is converted completely into the gaseous state before it is fed into the powder cavity (1). The propellant is dried to some extent. This prevents liquid propellant from causing the powder to clump together. Clumped powder disperses substantially less well and the pulmonary delivery of the aerosol particles produced during the nebulisation deteriorates. Video images with a high-speed camera by means of which the interior of the powder cavity (1) has been observed through a transparent base of the powder cavity (1) during the feeding of propellant demonstrate that the clumping referred to above occurs if no vaporiser (6) is used, whereas when the vaporiser described in detail hereinafter is used no agglomeration or clumping can be detected.

Figure 3A:
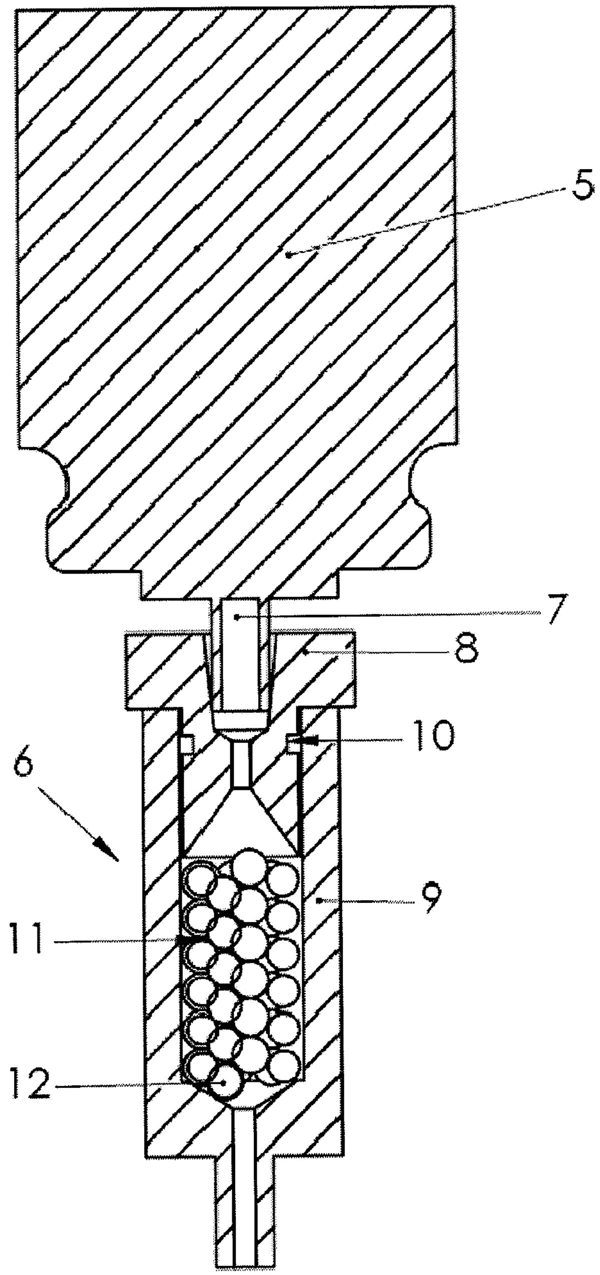
FIG. 3*a* shows a schematic section through a part of the propellant feed device of FIG. 2
Figure 3B:
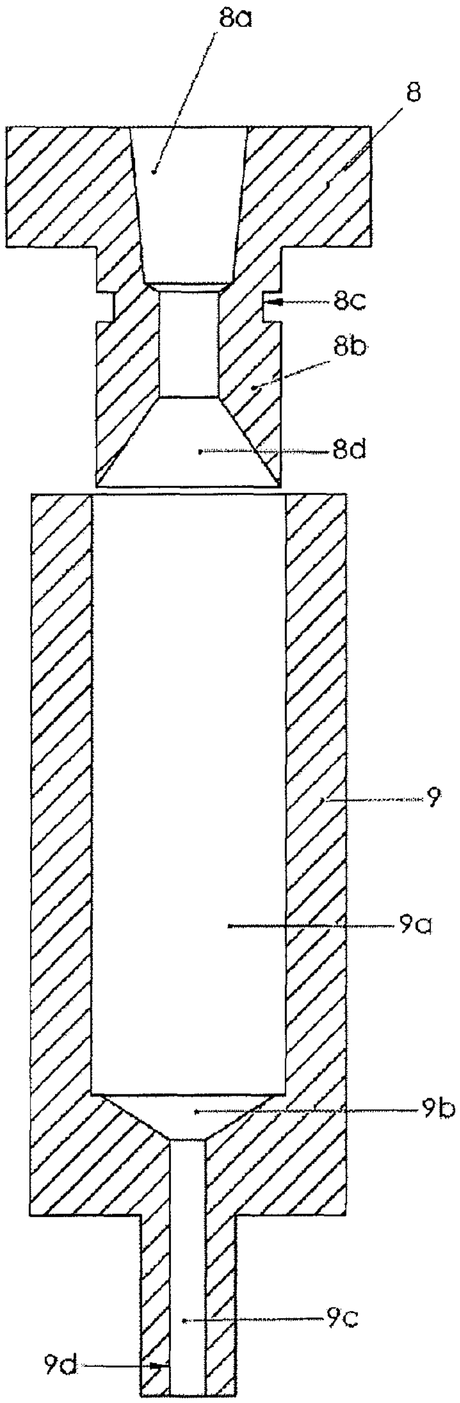
FIG. 3*b* shows a schematic section through two individual components of the propellant feed.

FIG. 3 shows a possible design of a vaporiser (6) of this kind. In the embodiment shown for use in a test device the inlet of the vaporiser (6) is configured such that on the one hand it comprises a receptacle (8*a*) for a standard commercial valve stem (7) of a cartridge (5) and on the other hand the outlet (9*c*) is configured so that the exterior of the vaporiser (6) at this point is precisely in the form of a stem (9*d*) with the same dimensions as in a standard commercial valve stem, for example a diameter of 2 millimeters. Accordingly, the connector (4) also has a valve stem receptacle to which the vaporiser (6) or, if desired, the cartridge (5) can be connected for test purposes as shown here. The vaporiser (6) shown, which is preferably rotationally symmetrical, comprises a body (9) with a preferably cylindrical cavity (9*a*). The base of the cavity is preferably shaped like a funnel (9*b*) from the centre of which the outlet (9*c*) extends as a channel. The cavity (9*a*) of the vaporiser is closed off by a cover (8), the flange (8*b*) of which extends into the upper region of the cavity (9*a*). Preferably, the body (9) and the cover (8) of the vaporiser (6) are sealed off from one another by means of a seal (10). This seal (10) is for example an annular component of elastomeric material in a rotationally symmetrical vaporiser (6). The seal is placed for example in a crimp (8*c*) on the flange (8*b*) of the cover (8). The cover comprises a valve stem receptacle (8*a*) that adapted to receive a valve stem of a standard commercial cartridge (5) and a passage which preferably opens towards the cavity (9*a*), via an inner cone (8*d*). Preferably, an additional seal, for example in the form of an "0" ring, is mounted on the upper part of the valve stem (7), so that no ambient air travels along the valve stem (7) through the valve stem receptacle (8*a*) into the system.

The action of the vaporiser (6) is based on heat exchange mechanisms. The vaporiser (6) itself is preferably made of metal and the cavity is preferably also filled with metal components, which are referred to hereinafter as heat exchange elements. The propellant kept liquid under pressure in the cartridge (5) evaporates under normal pressure, above about −25° C. in the present embodiment. Thus if it is able to expand in the cavity of the vaporiser (6), it changes from the liquid state into the gaseous state. The heat exchange elements assist or accelerate this evaporation by giving off heat to the propellant flowing along them. The heat exchange elements preferably have the largest possible surface area for this reason. This increases the entire inner surface area of the vaporiser, i.e. the contact surface for the heat exchange mechanism, and reduces the dead volume, i.e. the empty space inside the vaporiser.

Metals are the preferred material for all the components of the vaporiser, as they have a high heat conductivity and consequently favour the evaporation of the propellant coming into contact with them. It is possible to use most of the metals that are solid at ambient temperature, stainless steels being particularly preferred as they are compatible with the majority of propellants, provided that no constituents of the metal are absorbed by the propellant and fed into the nebulisation. Noble metals such as silver and gold are also highly suitable but are usually ruled out on cost grounds. Both for the body (9) of the vaporiser (6) and for heat exchange elements in its cavity (9*a*) aluminium, stainless steel or copper are specifically preferred materials. In one embodiment used in tests, the body (9) of the vaporiser (6) is made of aluminium and the cavity (9*a*) is filled with beads (11) of stainless steel. Depending on the evaporation characteristics of the propellant chosen, it may on occasion be sufficient if only the heat exchange elements are made of metal and the body (9) itself is made of plastics. This has cost advantages during production. The vaporiser may be varied in terms of its length and hence the number of heat exchange elements as well, in order to be adapted to the quantity of propellant used. Thus, when small amounts of propellant are used, a smaller or shorter vaporiser may be used. In the course of tests, in conjunction with metering valves that release 50 microliters of propellant, a vaporiser (6) with an inner space 6 millimeters long and filled with 27 steel beads 2 millimeters in diameter was used, for example. In conjunction with 100 microliter valves a 12 millimeter long vaporiser (6) with 48 beads (11) was used. This ratio of vaporiser length or number of beads (11) to the volume of the metering valve used can be scaled up or down as desired—including for larger metering valves.

To ensure that none of the beads (11) displaces the outlet (9*c*) in the bottom of the funnel (9*b*), in the specific embodiment shown there is a coiled wire (12) in the funnel (9*b*), made of copper, for example, which keeps the beads (11) away from the outlet (9*c*). If desired the metal beads can also be replaced by a long, thin, coiled metal wire in the cavity (9*a*). In the embodiment shown, the beads (11) have a diameter of 2 millimeters, and opposite them is an outlet (9*c*) with a diameter of 1 millimeter.

The configuration or arrangement of the components as a whole is selected such that on the one hand the vaporiser (6) has the largest possible inner surface for efficient vaporisation of the propellant but on the other hand the filling with heat exchange elements has a sufficient number of small free cross-sections so that its flow resistance does not become so high, i.e. so that it does not slow down the propellant passing through it too much. In this context a flow resistance of about 465000 $\sqrt{N^*s/m^4}\pm10\%$ is preferred, in relation to air (the flow resistances for propellant may be expected to be even lower than for air. This corresponds to a flow of 10 liters per minute occurring with a pressure drop of 6 kilopascals (a flow of less than 5 liters per minute with a pressure drop of 6 kilopascals would constitute a less favourable flow resistance, for example, with the propellant gas being significantly slowed down on its way through the vaporiser). The flow resistance of the vaporiser is influenced by its geometry and by the size and shape of the heat exchange elements contained therein. In the configuration preferred here, the interstices between the beads make it possible to achieve a good flow through the vaporiser, the contours in transitional regions are fluidically favourable as a result of the use of cone structures and the spherical shape of the heat exchange elements also helps to ensure that there is little or no turbulence in the flow. As a result, there is only a small drop in the pressure of the propellant in the vaporiser, and therefore the flow of gas is slowed down only a little. This is advantageous in that a high propellant sped is essential for good dispersion of the powder.

The speed of the propellant on entering the powder cavity (1) may be influenced, particularly constricted, by the size of the diameters of the feed channels. In the case of the test device, different connectors (4) with different feed channel widths can be tested. With the measured results that form the basis here, channel diameters ranging from 0.2 to 2 millimeters between the vaporiser (6) and powder cavity (1) were tested, with diameters ranging from 1 to 2 millimeters proving particularly suitable. In the case of an inhaler suitable for mass production, it is advisable for reasons of cost to connect the vaporiser (6) with a suitably sized outlet (9*c*) directly to the powder cavity (1).

On the one hand, a high propellant speed on entering the powder cavity (1) is advantageous in terms of the dispersion of the powder and hence for the inhalability of the aerosol particles expelled by the nebuliser, but on the other hand it is not desirable if the entire nebulisation process is completed within a small fraction of a second. (According to observations taken with a high speed camera, a propellant gas cartridge with a 100 microliter valve sprays for about 50 to 60 milliseconds.) This would make it difficult for a patient to coordinate his breathing with the production of the aerosol that is to be breathed in. Therefore, a process has been developed here for dividing the nebulisation process into a number of short nebulisation processes and to combine these in a time interval that corresponds in its duration to one inward breath of a patient. A time interval that is suitable for such coordination is of the order of 1 second. By breaking the nebulisation down into a plurality of staggered processes, the release of aerosol as a whole can be slowed down, while the propellant itself enters the powder cavity (1) at the high speed that is suitable for the dispersion of the powder. Various constructions will be described hereinafter, which are suitable for delivering a plurality of successive bursts (pulses) of propellant.

Figure 4A:
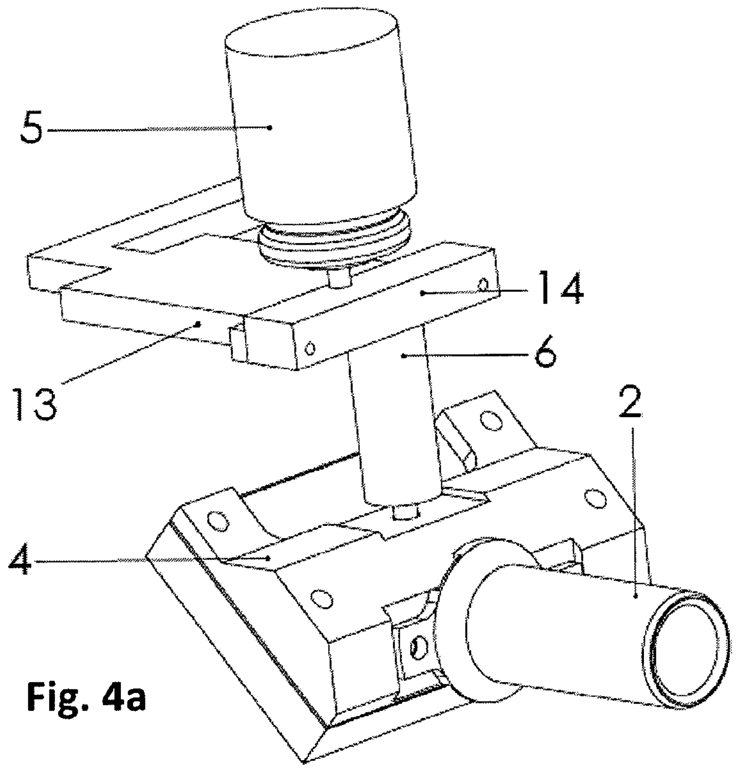
FIG. 4*a* shows a nebuliser according to the invention embodied as a test device with a controlled valve in the propellant feed.

The flow diagram in FIG. 4*a* shows an arrangement in which propellant from a cartridge K is fed in pulses to a nebuliser I for producing the aerosol A. The liquid propellant from the metering valve of the cartridge K is conveyed to a hydraulic magnetic valve (for example, a standard commercial 2/2-way flipper magnetic valve). The magnetic valve V opens and closes in a matter of milliseconds and thereby releases a quantity of propellant defined by the opening time into the vaporiser or heat exchanger WT connected to the nebuliser I. The duration of the opening time, the number of pulses and the time interval between them are adjusted by means of a standard commercial pulse generator G which is used to control the magnetic valve V. In this arrangement the jets of propellant are metered in fluid form. Metering of the propellant after it has been vaporised would also be possible in theory, but has the disadvantage that in every pulse the residual volume of gas and the resulting pressure is decreased. A volume $V_1$ of 100 microliters of liquid propellant R134a has a density D at ambient temperature of 1210 [$kg/m^3$]. Because of the molar mass M of 0.1024 [kg/mol] the transformation according to $n=D^*V_1/M$ gives a quantity of substance n of 0.00118 mol. As an approximation, the ideal gas law $p=n^*R^*T/V_2$ gives a volume $V_2$ of about 28 milliliters for the dose of propellant converted into the gas state, at ambient temperature T, normal pressure p and with the ideal gas constant R. For particularly good dispersion of the powder onto which the pulses of propellant are directed in the nebuliser, it is advantageous to have pulses in the propellant that are defined as sharply as possible without any great variation in speed. Alternate stoppage of flow, followed by very rapid accelerations of flow, promotes dispersion and thus leads to improved delivery of the aerosol particles to the lungs, or a higher fine particle dose (FPD). The valve for producing the pulses of propellant is thus preferably capable of being opened and closed in an abrupt movement. In particular, the valve is selected such that the opening or closing actions take considerably less time than the delay between two pulses. The hydraulic magnetic valve with actuation by a pulse generator has proved suitable for this purpose. It would be comparatively far less suitable to have a completely different arrangement (not shown) in which it was attempted to pulse the propellant in the form of liquefied gas from a cartridge (5) by conveying it into rotating cavities of 7 to 23 microliters in volume (after a cartridge metering valve with a volume of 100 microliter) and then to deliver the propellant from the cavities into the nebuliser system. By using rotating cavities of this kind (provided between the cartridge (5) and the vaporiser (6), rotation assisted by an electric motor, for example), it was admittedly possible to improve the emptying of powder cavities (1) a little during measurement (up to 10% improvement in values at higher speeds in the measuring range between 700 and 2000 revolutions per minute and at smaller volumes of the cavity); however, this slight improvement in the powder delivery was accompanied by a significant deterioration in the dispersion of the formulation to be delivered (30% lower inhalable fraction of active substance). The reasons for the poorer dispersion were presumably, on the one hand, that the arrangement slowed down the speed of the propellant, affecting the quality of nebulisation, and on the other hand that the pulse generating device was not completely gas-tight because of the need for rotatability and therefore the stream of propellant never stopped completely between the pulses (the pulses generated with this rotating arrangement thus constituted an oscillation of a stationary stream of propellant).

However, when a magnetic valve arrangement is used (according to FIG. 4*a* and FIG. 4*b*) the pulses can be measured without causing permanent residual flows of propellant or a significant deceleration of the propellant gas itself. For the measurements carried out with the magnetic valve arrangement within the scope of this development, at least 100 milliseconds delay was set between two pulses as a result of the technical data of the magnetic valve and its actuation. With the proviso that the time of the propellant delivery was extended to approximately one whole second, propellant from 100 microliter-metering valves was broken down into 12 to 5 pulses for valve opening times of 7 to 30 milliseconds, and propellant from 50 microliter-metering valves was broken down into 5 pulses for a valve opening time of 7 milliseconds.

Figure 4B:
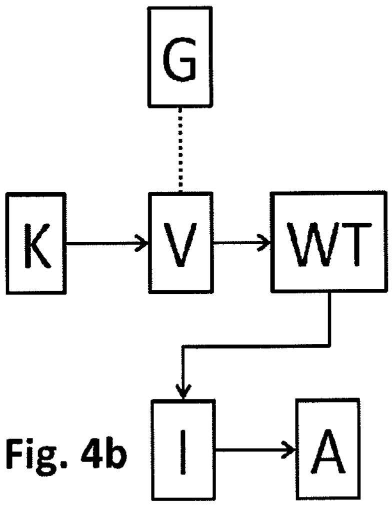
FIG. 4*b* shows a flow diagram relating to the processes in the nebuliser of FIG. 4*a*.

FIG. 4*a* shows a nebuliser embodied analogously to FIG. 2 as a test device, actuated according to FIG. 4*b*. The cartridge (5) is connected by its valve stem (7) to a corresponding connecting point of a flange plate (14). The propellant from the cartridge is supplied through a channel in this flange plate (14) to a standard commercial magnetic valve (13) or magnetic valve unit. The transition between the flange plate and the magnetic valve unit about the inlets and outlets can be sealed off, with a suitable choice of material (e.g. two plastics) by firmly pressing the flange plate (14) and magnetic valve unit against one another or by additionally inserting sealing elements between the flange plate (14) and the magnetic valve unit. Connecting members are channel up to the magnetic valve (13) are designed to that their internal volume is able to hold the quantity of propellant released when the valve of the cartridge (5) is actuated, i.e. this internal volume is at least 100 microliters, for example, when using a 100 microliter metering valve in the cartridge (5). Thus, after the actuation of the metering valve, the entire quantity of propellant provided for the expulsion of a dose is directly present at the magnetic valve (13). In addition, however, the channels in the flange plate (14) are so small and short that the dead volume therein is kept as small as possible. By suitably setting the attached pulse generator, the quantity of propellant contained in the flange plate (14) is then released in batches through the magnetic valve (13), so as to produce the propellant pulses according to the invention. The shorter the opening times of the magnetic valve (13), the smaller the volumes of propellant that are separated off or divided into portions, and the more pulses of propellant are produced. With the measurements used here as the basis, opening times $t_1$ in the range from 7 to 40 milliseconds and closure times $t_2$ in the range from 100 to 200 milliseconds are used, for example. The attached diagram in FIG. 4*d* shows the dependency of the expulsion from a powder cavity filled with 50 mg of the formulation containing 32.5% active substance as an extrapolation from the corresponding measurements obtained. According to this, particularly good expulsion of the powder would be obtained with opening times $t_1$ in the range from 13 to 24 milliseconds, particularly with longer closure times $t_2$, particularly with closure times $t_2$ above 160 milliseconds. However, over all, the influence of the closure time $t_2$ tends to increase with shorter opening times $t_1$ (thus, short pulses are presumably most effective in expelling the powder from the cavity when all the flows produced by the individual pulses in the cavity have come to a complete standstill between the pulses). This diagram also shows how much the pulsing of the propellant can improve the delivery of the powder from the powder cavity (1): comparative measurements for the same cavity (tub-shaped cavity according to FIG. 7*a,* 3 millimeters deep), with the same filling and using the same nozzle (0.5 millimeter diameter of the nozzle channel (3*a*)), showed that the use of propellant pulsing can increase the emptying of the cavity from about 66% (without pulsing) to 86%.

The comparatively very high fine particle content values for the delivered dose were achieved with the shortest opening times $t_1$ of 7 or 10 milliseconds, while additionally the fine particle content was apparently hardly dependent at all on the closure time $t_2$. For this reason, and because it is desirable in the interests of better coordination of a breathing process with the pulse sequence for the entire sequence to be no longer than 1 second, the use of opening times $t_1$ in the region of only 7 milliseconds and closure times $t_2$ of only about 100 milliseconds is well suited to the use of the nebuliser as an inhaler.

The outlet of the magnetic valve unit is in turn connected to another channel in the flange plate (14) and this additional channel leads to an outlet which is configured such that the vaporiser (6) can be directly connected thereto. Preferably, the outlet on the flange plate (14) is configured for this purpose as a cover (8) for the vaporiser (6), so that the body (9) of the vaporiser (6) can be connected directly to the flange plate (14). This contributes to the short configuration of the channel paths between the magnetic valve (13) and vaporiser (6) and hence to a reduction in possible dead volumes. In its embodiment as a cover (8) of the vaporiser (6) the outlet on the flange plate (14) has a projection with a central channel opening, this projection fitting straight up into the body (8) of the vaporiser (6). For the embodiment of a radially symmetrical vaporiser (6) according to FIGS. 3*a* and 3*b* this means that the outlet on the flange plate (14) is embodied as an externally cylindrical projection. On the inside, this outlet preferably has an inner cone (8*d*) through which the propellant conveyed to the vaporiser (6) is distributed as widely as possible over the heat exchange elements or the beads (11) of the vaporiser (6). In the construction as a test device, the outlet of the flange plate (14) may alternatively also have the form of a valve stem (7), which for comparison purposes can be connected to any desired modules of the test device. With such a configuration it would naturally not be possible to do without the original cover (8) of the vaporiser (9), but instead the cover (8) would be used as the connector. Preferably, the flange plate (14) is made from a plastics that is resistant to the propellant, for example PEEK (polyether ether ketone). In particular, the connecting plate (14) should not be made of metal, to ensure that the propellant evaporates as little as possible before entering the vaporiser (6) or passes through the magnetic valve (13) in the liquid phase.

Figure 4C:
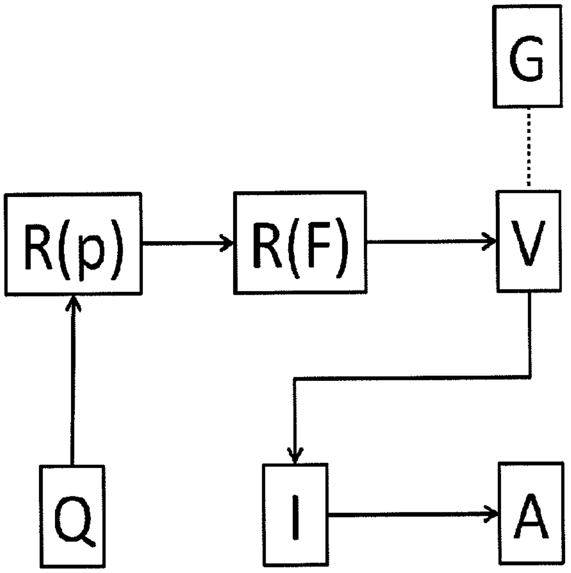
FIG. 4*c* shows a flow diagram relating to the connections of an alternative propellant-driven nebuliser and FIG. 4*d* shows a diagram with extrapolated measurements for emptying the powder cavity as a function of opening and closing times $t_1$ and $t_2$ set at the valve for an arrangement according to FIG. 4*a*, FIGS. 5*a, b, c* and *d* show different microstructured channel structures for generating pulses in flows.
Figure 4D:
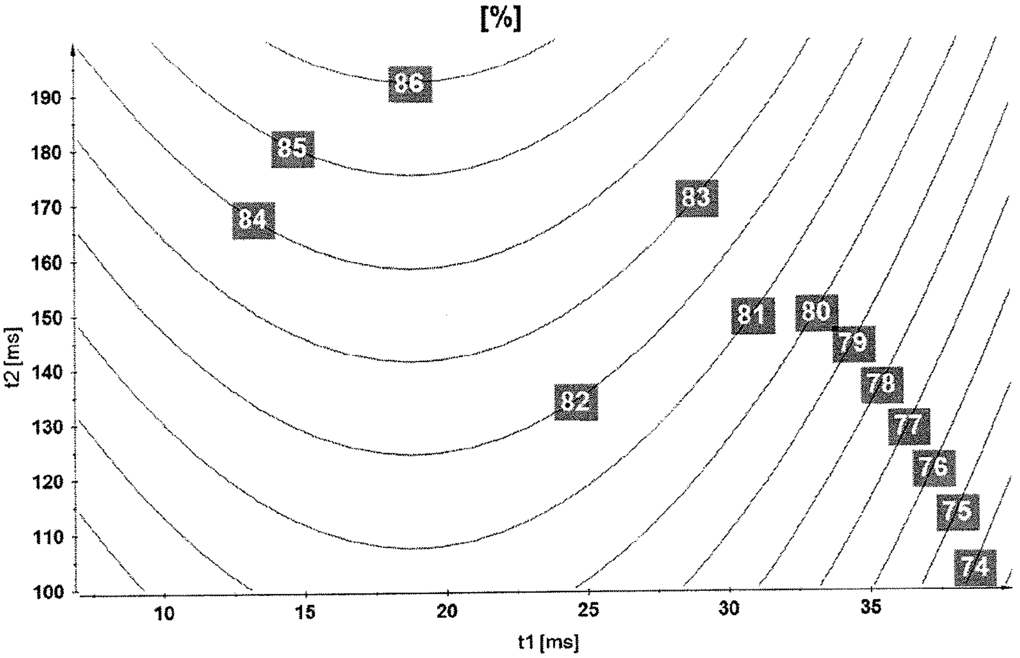

FIG. 4*c* shows a flow diagram of the operation of a nebuliser assisted by propellant gas. As an alternative to the mounting of a cartridge (5) filled with propellant in liquid form, in this embodiment, a nebuliser is operated with gaseous propellant. In principle, gaseous propellant such as compressed air or nitrogen can be conveyed directly into a powder cavity as it does not contain any liquid constituents. Then there is no need to use a vaporiser. As a rule, arrangements with pressurised gas lines and/or gas bottles connected to them are so complex that they are only suitable for use as a free-standing apparatus, e.g. in a laboratory, but are not suitable for portable hand-held devices. This system is particularly suitable for example for carrying out tests on the influencing the variation of factors such as the number of pulses, the closure time and the pressure. FIG. 4*c* schematically shows how a propellant gas is conveyed from a source Q (for example, a standard laboratory nitrogen or compressed air line or a gas bottle) through a pressure regulator R(p) and a flow regulator R(F) to a pneumatic magnetic valve V. With the flow regulator R(F) a flow of constant strength is also achieved at different pre-set pressures. The air flow is measured with a standard commercial flow meter. The magnetic valve V downstream thereof opens and closes in a matter of milliseconds and thereby releases a quantity of nitrogen into the nebuliser I defined by means of the opening time, from which the aerosol A is subsequently released. By means of a pulse generator G, which is used to control the magnetic valve V, the duration of the opening time, the number of pulses and the time interval between them are set.

When the magnetic valve V of the arrangement according to FIG. 4*a* is opened 100 microliters of liquid propellant are released from a cartridge in about 50-60 milliseconds (as demonstrated by images taken with a high speed camera). For better comparability of measurements, also when using a source Q, the same volume of gas can be obtained as with a jet of propellant gas from the cartridge of 100 microliters per actuation and using pulses a spray time extended to up to 1 second can be achieved and has the following opportunity, for example, of adjusting the pulse jets for the previously calculated propellant volume of 28 milliliters:

| number of pulses | opening time of the magnetic valve in milliseconds | maximum delay between the pulses in milliseconds |
|---|---|---|
| 1 | 50 | — |
| 2 | 25 | 500 |
| 3 | 16.7 | 330 |
| 4 | 12.7 | 200 |
| 8 | 6.25 | 125 |
| 9 | 5.2 | 110 |
| 16 | 3.125 | 60 |

For the measurements carried out within the scope of this development a delay of at least 50 milliseconds was set between two pulses, i.e. a closure time $t_2$ of 50 milliseconds between two opening times $t_1$ of the valve. In the measurements, the number of pulses was varied in the range from 1 to 16 and the closure time $t_2$ was varied within the range from 50 to 400 milliseconds. A trend of better emptying of the powder cavity (1) with an increasing number of pulses (associated in this case by shorter opening times) and an increasing closure time between the pulses was observed. Good results in terms of the delivery of powder from the powder cavity were obtained accordingly at a medium setting—extrapolated part for the range of 7-10 pulses with a 200 to 100 millisecond delay. This number of pulses corresponds to opening times $t_1$ of 5 to 7 milliseconds in relation to the arrangement shown in FIG. 4*a.*

Tests with variations in the pressure of the propellant gas in the range between 2 and 6 bar and variations in the numbers of pulses in the range from 1 to 16 showed, by means of a powder cavity (1) with an internal capacity of 0.19 milliliter (corresponding to 45 milligram lactose or 50 milligram of the lactose-based formulation with 32.5% active substance), that both the delivery of the powder from the powder cavity (1) and the fine particle content of the expelled particles increases as the pressure rises. The effect of pressure particularly on the fine particle content increases to begin with as the number of pulses rises. For the range of 7-14 pulses (corresponding to opening times 7 to 4 milliseconds) the test results showed the highest values at higher pressures. In this pulse range, presumably pressure peaks were able to occur in the powder cavity, which are particularly favourable for the breaking up of the particles. At higher numbers of pulses, the influence of the pressure appears to decrease again (presumably the valve opening times are then too short to enable the full degree of pressure in front of the valve to build up again behind the valve).

In all, the aerosol measurements that were obtained using the nebuliser devices with pulsed propellant feed as described hereinbefore showed that by using a large number of pulses and long delay times between the pulses, it is possible to increase the delivery of active substance and the fine particle content of the delivered dose. Comparative measurements showed an increase in the fine particle content to a value corresponding to about 130% of the value achieved with a corresponding device without a magnetic valve.

In all, with the measurements on which this specification is based, using both a magnetic valve (13) for pulsing the propellant and also a vaporiser (6), very large amounts of powdered formulations were able to be expelled from powder cavities (1): thus, for example, it was possible to obtain 16.5 milligram of fenoterol as the fine particle content from 75 milligrams of a powder mixture containing 98% fenoterol (with 92.5% emptying of the powder cavity, at an applied flow rate of 30 liters per minute). When a propellant-driven device of this kind with a vaporiser and magnetic valve is used, the strength of the flow rate applied to the mouthpiece of the nebuliser, within the scope of the measurements carried out here, did not appear to have any significant influence on the fine particle content of the delivered dose (flow rates tested varied in the range from 30 to 90 liters per minute).

Figure 5A:
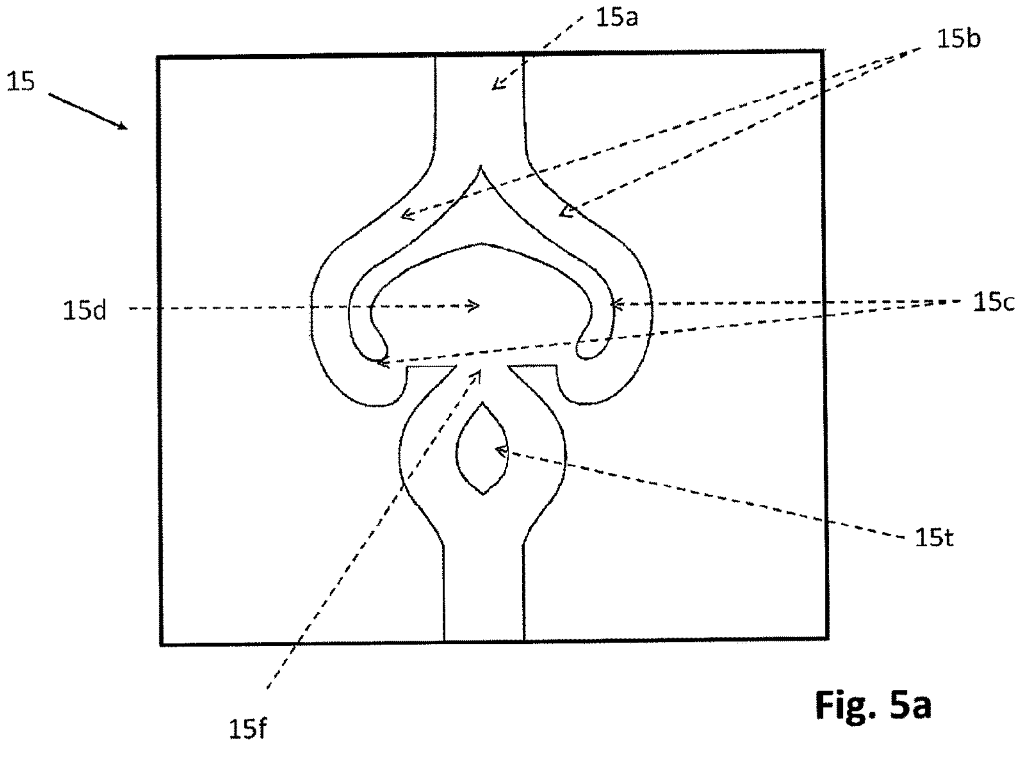
Figure 5B:
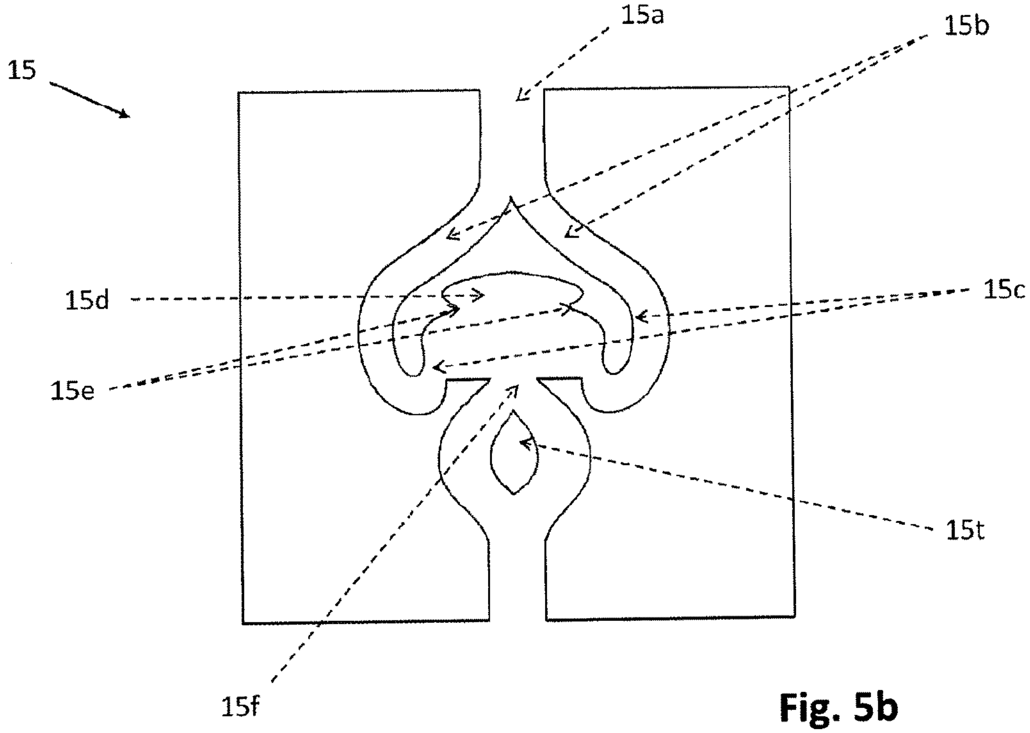
Figure 5C:
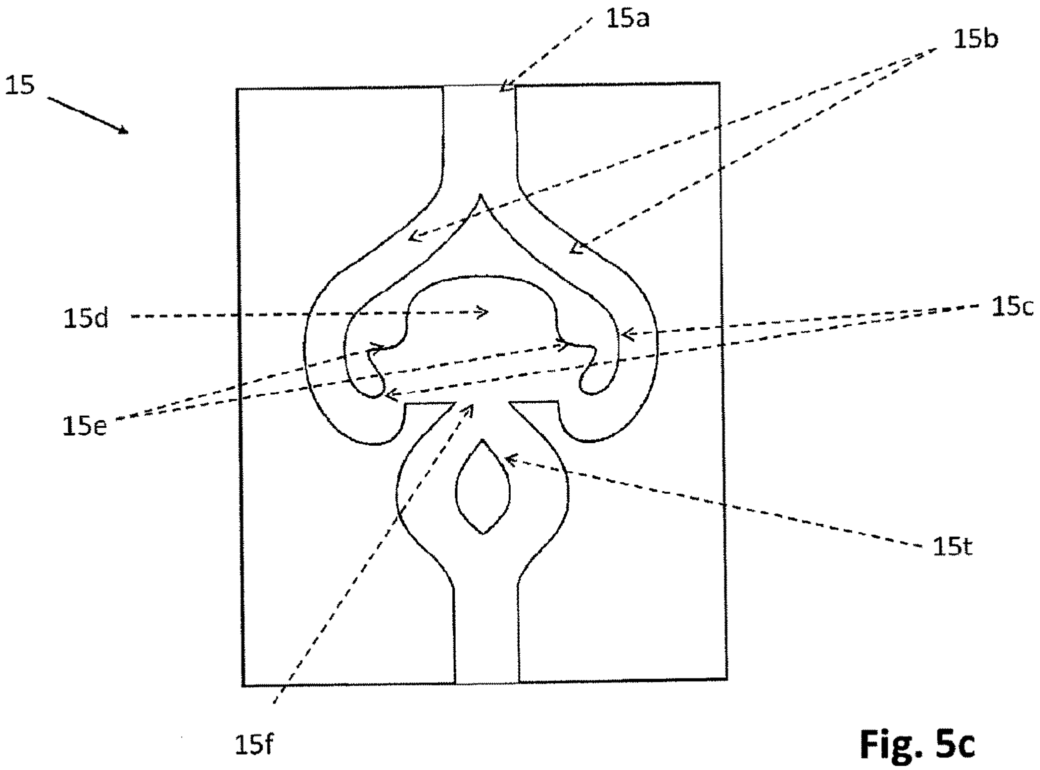

FIGS. 5*a, b* and *c* show various channel structures each forming a microfluidic oscillator (15), of the kind that may be inserted in the propellant feed of a nebulisation device, as an alternative to the magnetic valve (13) described by reference to FIG. 4. Preferably, this microfluidic oscillator (15) is also located in the flow path between the cartridge (5) with metering valve which is filled with propellant or liquid propellant gas, and the vaporiser (6) upstream of the feed line into the powder cavity (1).

The flow path in FIGS. 5 *a-d* is illustrated from the top downwards. In an installed position the outlet of the metering valve of the cartridge (5) is connected to the inlet channel (15*a*) of the channel structure. In the embodiments of the microfluidic oscillator (15) shown in FIGS. 5*a*, 5*b* and 5*c*, the inlet channel (15*a*) forks into two partial channels (15*b*) at a fork. The fork is configured so that the liquid can hug the internal walls (15*c*) (in relation to the channel structure as a whole) of the partial channels (15*b*) with as little friction as possible. For this reason, the start of the fork may for example be V-shaped (as shown in FIGS. 5*a*, 5*b* and 5*c*) or of arcuate configuration, and in particular the fork is embodied to be symmetrical in relation to the axis formed by the inlet channel (15*a*). The entire channel structure preferably has a mirror symmetry about the axis formed by the inlet channel (15*a*). As they continue, the partial channels (15*b*) curve inwards and open into a mixing area (15*d*). At the same time they are preferably always guided along the inner wall, by the Coanda effect. Preferably, after entering the mixing region (15*d*), the flow is additionally deflected by the corresponding internal walls (by suitably chosen curvatures of the walls) at least slightly counter to the main direction of flow determined by the inlet and outlet of the channel structure. In the embodiment shown in FIG. 5*a*, the liquid flows are sent back in some cases to the upper edge of the mixing region (15*d*), the latest point where the flows from the two partial channels (15*b*) meet again. In the embodiment according to FIGS. 5*b* and 5*c* the fluid jets from the two partial channels (15*b*) are deflected towards one another into the mixing region (15*d*) by projections (15*e*) adjacent to the respective flow guidance portions of the wall of the mixing region. The purpose of these deflections is to create as much turbulence as possible in the mixing region (15*d*). As a result of this turbulence, the flow of the fluid through the opening of the outlet (15*f*) from the mixing region (15*d*), which may also be referred to here as the oscillation chamber, always stagnates, with precedence being given alternately to the flows from the two partial channels (15*b*), after which the flow also stops in the mean time. This behaviour could be clearly seen in flow simulations. Operation with liquefied propellant gas increases the "stagnation" by the formation of gas bubbles in the mixing region (15*d*). During the turbulence, areas of different densities are formed in the fluid in the mixing region (15*d*), so that superheating and the formation of gas bubbles occur. These gas bubbles then in turn contribute to a sudden expulsion of the fluid from the mixing region (15*d*). Optionally (but not necessarily), a flow distributor may be provided in the channel connected to the outlet (15*f*), this flow distributor alternately promoting, by the Coanda effect, one flow to the left for the flow from the partial channel (15*b*) that was originally on the right, and one flow to the right for the flow from the partial channel (15*b*) that was originally on the left.

Figure 5D:
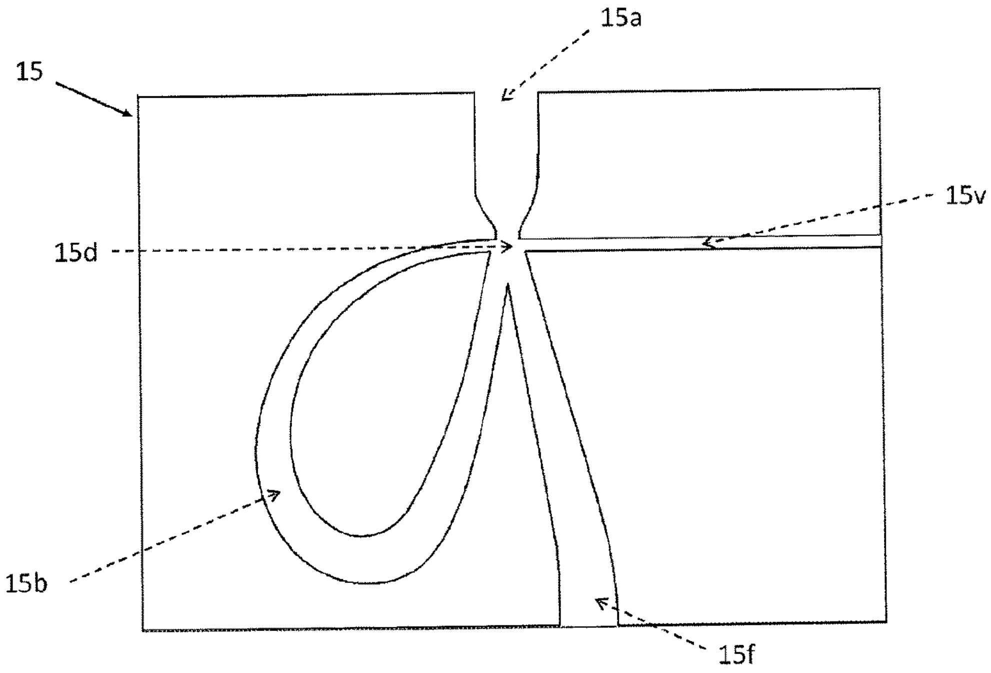

FIG. 5*d* shows an alternative microfluidic oscillator (15). In this embodiment, the inlet channel (15*a*) leads to a widened portion into which a control or ventilation channel (15*v*) can open from the sides. Adjoining the widened region is a channel fork, this fork branching into a partial channel (15*b*) and an outlet (15*f*). The partial channel (15*b*) is configured so that it is sent back laterally into the widened region (so to speak, in the manner of a feed channel) by the fluid passing through it. The widened region can thus also be referred to as a mixing region (15*d*). The symmetry of the inlet channel (15*a*) and the fork is again such as to promote flow into both branches of the fork equally, according to the Coanda effect. By means of a pressure gradient which is provided laterally through a ventilation channel (15*v*), for example, the flow can be influenced for example to flow first of all into the partial channel (15*b*). The re-emergence of this fluid jet as a feed into the widened region can then steer the preferential direction of the jet towards the outlet (15*f*), so that fluid briefly leaves the component, but because of the ventilation channel the preferential direction can be changed again into the direction of the partial channel (15*b*), so as to produce an oscillating system.

Beyond the representations of microfluidic components in FIG. 5*a-d* it is also possible to provide channel structures having a microfluidic oscillator, which are arranged at the outlet of the mixing region, for example, such that vaporisation of the fraction of the propellant that has hitherto not been gaseous occurs, so that an adjacent vaporiser (6) provided as an additional component in the flow path can be dispensed with, or is formed directly in the unit forming the channel structure. Possible ways of producing the channel structures described include for example silicon etching techniques, LIGA processes or other methods of producing microstructures, particularly microfluidic systems. In accordance with manufacturing methods of this kind, the channel structure shown here is preferably two-dimensional, i.e. it preferably consists of a plate in which the channels are formed with a right-angled cross-section, for example, a cover being fixed to the plate, thus closing off the channels longitudinally.

Figure 6A:
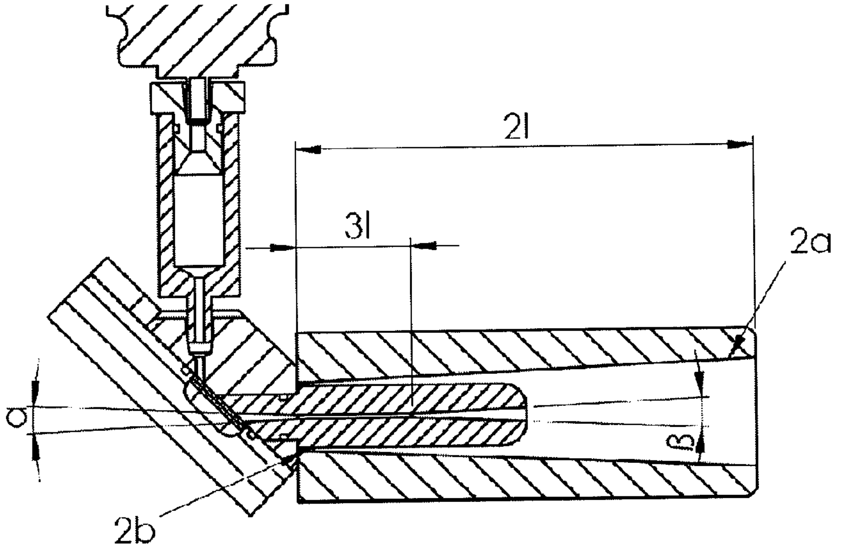
FIG. 6*a* shows a schematic section through the nebulisation unit of a device, while FIG. 6*b* and also the sectional view in FIG. 6*c* show a nozzle inserted in this device.

FIG. 1*a* shows how a feed channel in the connector (4) leads straight to the powder cavity (1) and how the nozzle channel of the nozzle (3), which will be described more precisely hereinafter with reference to FIG. 6 *a-c*, leads off directly from the powder cavity (1). Preferred powder cavity forms for this arrangement are shown in FIG. 7*a* and in FIG. 7*b* and FIG. 7*c*. FIG. 7*a* shows a carrier (1*t*), constructed especially for use in a test device according to FIG. 2, containing the powder cavity (1). Particularly for use in a test device the carrier (1*t*), or at least the part that forms the powder cavity (1), preferably consists of a transparent material such as PMMA, for example, so that it is possible to observe the emptying of the powder cavity (1) during nebulisation or during the feed of propellant, for example with a camera. The powder cavity (1) has a well (1*a*)—trough-shaped in the Figure—for holding the medicinal formulation or the powder. The opening of the well (1*a*) is surrounded on the upper side of the carrier (1*t*) by a sealing groove (1*b*), into which a sealing material such as, for example, a preferably elastomeric O-ring is placed, which, when the carrier (1*t*) and connector (4) are fitted together, seals off the interior of the powder cavity (1) all round in the region between the carrier (1*t*) and connector (4). The opening of the well (1*a*) in FIG. 7*a* has a substantially rectangular cross-section with rounded corners or an oval cross-section (not shown). Its length in the direction of flow is greater than its width; preferably, it is roughly twice as long as it is wide. The base is preferably rounded and/or cylindrically curved in the wall regions, so that the powder cavity (1) in the well (1*a*) does not have any corners in which powder could be deposited. In measurements with the test device described hereinbefore, wells (1*a*) of different sizes, in terms of their depth, were used: for the same cross-sections of opening, well depths of 1, 2, 3 and 4 millimeters were tested, adapted to the particular amounts of powder provided for nebulisation per powder cavity (1). 15, 30, 45 and 70 milligrams of lactose fitted into the corresponding wells (1*a*) (with a volume of for example 190 microliters for the 3 millimeter deep well (1*a*)). In the test measurements, better emptying characteristics were obtained with flatter wells (1*a*): when filled with lactose it was possible to achieve emptying levels of up to 85%, 80% and 70% for depths of 1, 2, 3 millimeters without any pulsing of the propellant. In the assembled state, a feed channel from the connector (4) opens out close to one end of the trough-shaped well (1*a*) and the nozzle channel (3*a*) is connected close to the other end of the well (1*a*).

Figure 7A:
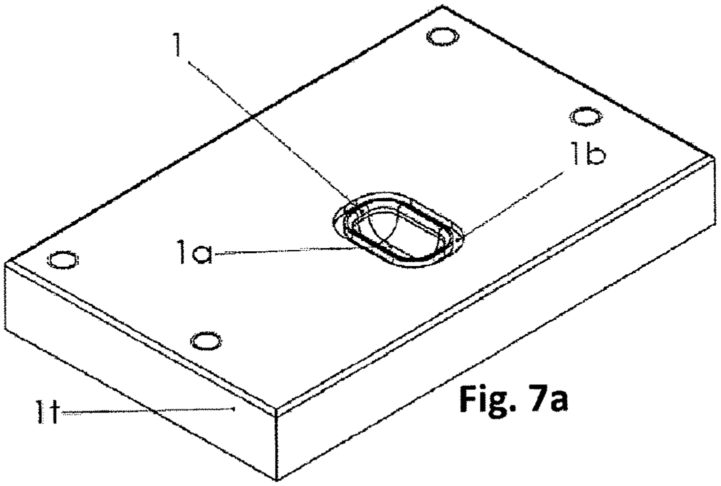
FIG. 7*a* shows a carrier with a tub-like powder cavity.
Figure 7B:
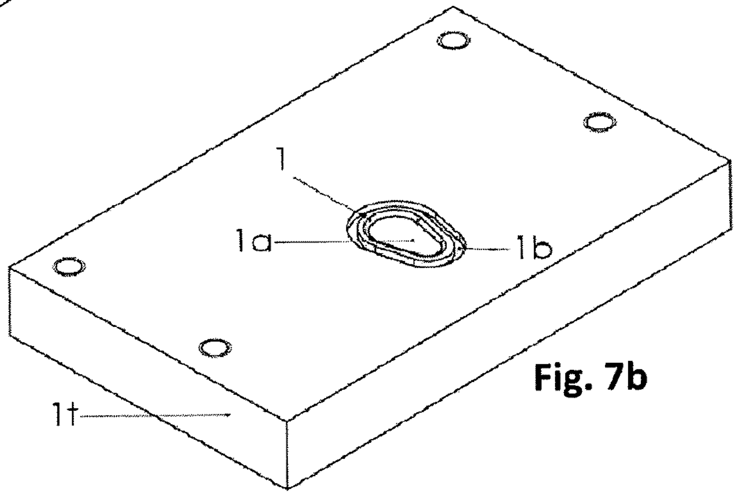
FIG. 7*b* shows a carrier with a teardrop-shaped powder cavity in plan view and FIG. 7*c* shows the teardrop-shaped powder cavity in schematic sectional view.
Figure 7C:
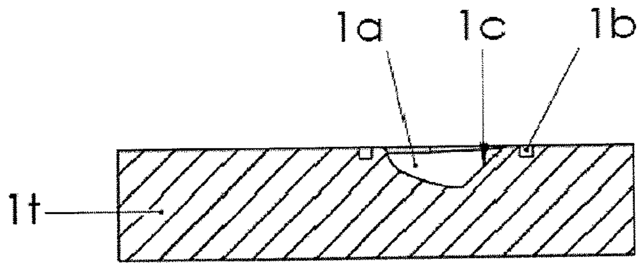

FIG. 7*b* and FIG. 7*c* show an alternative, preferred embodiment of the powder cavity (1). In many respects this embodiment has the same features (including their connections) as the embodiment described with reference to FIG. 7*a*, but deviates from it in that the well (1*a*) is now symmetrical only in the transverse direction but is no longer symmetrical in the longitudinal direction. The powder cavity (1) has a so-called teardrop shape. The "belly" of the teardrop is located close to the feed channel and the narrow end on the side where the nozzle channel (3*a*) is attached. Preferably, not only the opening of the well (1*a*), but also its base, is teardrop-shaped. Particularly preferably, the base of the well (1*a*) has a bottom point which is slightly displaced from the longitudinal centre in the direction of flow, this bottom optionally being configured as a small flattened area (1*d*), and adjoining this bottom point in the direction of flow is a slope (1*c*). This slope (1*c*) runs more steeply than the configuration of the base of the well (1*a*) before the bottom, viewed in the direction of flow. In this way, the flow already in the well (1*a*) is aligned with the adjoining nozzle channel (3*a*): As a result of the sharp convergence of the teardrop shape, the powder-laden flow is on the one hand made similar in its cross-section to the entry cross-section at the nozzle channel (3*a*) and on the other hand sent in the direction of the nozzle channel (3*a*) by the slope. Preferably, the slope (1*c*) forms the same angle, in relation to the surface of the carrier (1*t*), as the axis of the adjacent nozzle channel (3*a*), or preferably the direction of the slope (1*c*) continues in the direction of the nozzle channel (3*a*). In test measurements with lactose, teardrop-shaped powder cavities (1) of this kind showed higher emptying levels than the comparatively linear, tub-shaped powder cavities (1) (as described in relation to FIG. 7*a*). For teardrop-shaped powder cavities (1) up to 3 mm deep, even without pulsing of the jets of propellant, emptying levels of between 95% and 100% were achieved (for example 99.4% measured with nozzle cross-sections of 50 millimeters). As a rule, wells (1*a*) with a depth of 3 millimeters at the flattened portion (1*d*) and an internal volume of 50 microliters (corresponding to a capacity for 21 milligrams of lactose) were used. Adapted to the amount of powder provided for the nebulisation in each case, the depths of the teardrop-shaped wells (1*a*) may be varied analogously to those of the tub-shaped wells (1*a*) for example in the range from 1 to 5 millimeters deep or more, but because of their particular geometry, with the same maximum depth, they hold less powder than the tub-shaped wells (1*a*).

Figure 6B:
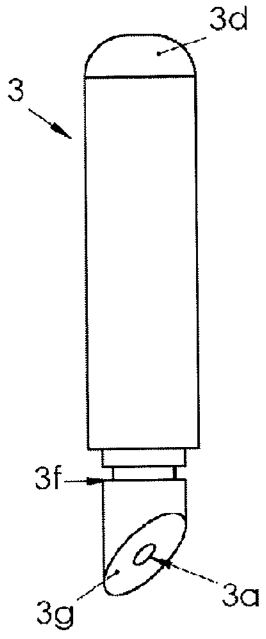
Figure 6C:
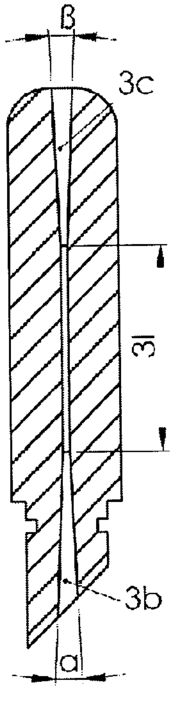

FIG. 6*b* and FIG. 6*c* shows the nozzle (3) in detail. It comprises a central nozzle channel (3*a*) which opens at the beginning into an inlet cone (3*b*) with an inlet angle α and towards the end into an outlet cone (3*c*) with an outlet angle β. α and β are preferably both 5°, but other angle sizes, different from one another, are also possible. Between these two cones the nozzle channel (3*a*) has a so-called cylindrical region in which the cross-section is constant over a defined length (3*l*).

The connecting side (3*g*) by which the nozzle (3) in the embodiment of the test device shown is placed against the powder cavity (1) is bent, according to the geometry of the connector (4), relative to the axis formed by the nozzle channel (3*a*), preferably through 45° in this instance. At this angle the propellant also strikes the powder cavity (1) at an angle of 45° beforehand, but other, flatter, angles are also possible. It is advantageous to design the exit of the nozzle channel (3*a*) from the powder cavity (1) as a mirror image at the same angle as the feed of propellant. This mirror image configuration is matched to the nozzle (3) attached to the powder cavity (1) and its particular rectilinear construction. When another nozzle (3) is chosen, such as, for example, a vortex nozzle or a nozzle the function of which defines a preceding vortex chamber, this rectilinear arrangement may not be present, in certain circumstances. When a nozzle with a vortex chamber is used (not shown in the drawings), contrary to what was stated above, it is expedient if the powder cavity (1) itself forms a vortex chamber, i.e. has a circular diameter, for example, preferably with a flat bottom, and the stream of propellant enters close to the edge of the powder cavity (1). The outlet of the nozzle is then located centrally above the powder cavity (1). Tests with vortex chambers of this kind were also carried out in this way using the test device described herein, but with the comparatively large amounts of powder measured here, because of high residues in the powder cavities, the tests yielded worse nebulisation results (emptying levels of only 60%) than the nozzle arrangements described in more detail with reference to FIG. 6 in conjunction with the powder cavities (1) described with reference to FIG. 7.

After leaving the nozzle (3) the powder is carried along by the air flow in the mouthpiece (2). In laboratory measurements with the test device, this air flow, which is produced in the inhaler by the patient's inward breath, is reproduced by a flow generating system. In both cases an air flow in the mouthpiece (2) is produced by an intake of air at the end of the mouthpiece (2) as a result of air being able to enter the mouthpiece (2) or the device through at least one inlet opening (2*b*) at an opposite point. Preferably, the inhaler or the test device comprises in the region of the nozzle (3) and mouthpiece (2) one or more channels connected to inlet openings (2*b*) which open into the mouthpiece (2) such that the air flowing through the channels envelops the stream of propellant leaving the nozzle (3) and thus carries the constituents along in a particularly suitable manner. In particular, these channels form a bypass to the nozzle. The aerodynamic diameter of this bypass—particularly at its narrowest point—determines the inspiration resistance experienced by a patient when inhaling from an inhaler of analogous construction.

The test device was used to carry out measurements in which an intake of air with flow rates of 30, 60 and 90 liters per minute was applied to the mouthpiece (2), thereby reproducing different breathing characteristics of patients. (30 liters per minute is the rate specified in the European Pharmacopoeia for the aerodynamic evaluation of metered-dose aerosols, while 90 liters per minute correspond to a negative pressure of 4 kilopascals in a passive powder inhaler.) The FPD results showed that for this nebulisation concept (delivery of dry powder through a straight, elongate nozzle channel by means of propellant dried in a vaporiser) the nebulisation showed no appreciable dependency on the breathing behaviour (even without pulsing of the propellant). Based on the total amount of active substance expelled from the nebuliser, at a flow rate of 30 liters per minute, rather greater deposits were found in the entry region of the attached measuring device (this entry region corresponds, with some limitations, to the oro-pharyngeal cavity of a patient when these measured results are applied to the use of an inhaler). At the flow rates of 60 and 90 liters per minute, the nebulisation characteristics showed no significant difference in terms of the total amount of active substance expelled. These higher flow rates are clearly better suited to picking up even the larger particles of the aerosol. In all, the nebulisation data for the concept proposed here show a significantly lower flow rate dependency than most commercially obtainable powder inhalers.

Preferably, as shown in FIG. 6*a*, the nozzle (3) or the module that forms it has been pushed into a passage (2*a*) at the mouthpiece (2) and the channels are located between the module that forms the nozzle (3), and an inner wall of the mouthpiece (2). Particularly preferably, the nozzle and mouthpiece are of substantially radially symmetrical configuration and are arranged relative to one another such that a substantially annular channel (albeit interrupted by mounting elements between the nozzle (3) and mouthpiece (2)) is provided between the nozzle (3) and mouthpiece (2). Optionally the annular thickness of the channel tapers towards the inlet opening (2*b*). This is further intensified in one embodiment (not shown) in which the nozzle is also conical on the outside, the conical slope of the nozzle (3) being embodied to be the opposite of the conical slope of the passage (2*a*) at the mouthpiece (2) (i.e. the widest point of the component that forms the nozzle (3) is located at the narrowest point of the passage (2*a*)). Preferably, the passage (2*a*) at the mouthpiece (2) is conical in form, opening in particular with an angle of 0° to 35° and particularly preferably with an angle of 0° to 15°, for example 5°, towards the end of the mouthpiece (2), where the suction is applied during use or in operation. Measurements of the fine particle dose (FPD) showed that the fine particle content increases when the smaller cone angles are used in the mouthpiece (as compared with the use of the larger cone angles), i.e. the pulmonary delivery of the nebulised particles is improved.

Preferably, the opening of the mouth tube (2) at the site of the outlet of the nozzle is significantly greater than the opening of the nozzle outlet, preferably at least 5 times as great, in relation to the diameter. This favours the aerodynamics in the mouth tube.

Preferably, the mouthpiece (2) at the said end is longer than the inserted nozzle (3). With varying lengths (2*l*) of the mouthpiece (2) from a total of 15 to 120 millimeters, it was found (for a fixed shorter length of the nozzle (3) of preferably not more than 15 millimeters) that with the shorter mouthpieces there were certainly smaller deposits of formulation on the wall of the passage (2*a*), but on the other hand, with the longer mouthpieces, the nebulisation mist had better aerodynamics. With the longer mouthpieces (2) (particularly those with a length (2*l*) of 120 millimeters) measurements showed an increase in the fine particle dose (FPD). Presumably, the flow in the mouth tube leads to favourable deceleration of the particles accelerated by the propellant gas, so that when a nebuliser of this kind is used there is an increase in the possible deposition of these particles in the patient's lungs.

With these two competing effects (formation of deposits inside the mouthpiece (2) and increase in the fine particle content of the aerosol) a preferred length range for the mouthpiece (2) is obtained, namely 30 to 90 millimeters, particularly preferably 60 to 90 millimeters, or a projection of the mouthpiece (2) beyond the end of the nozzle (3) by 20 to 70 millimeters, particularly preferably by 40 millimeters.

In the embodiment of the test device shown the nozzle (3) is inserted in the connector (4) so as to be sealed off by a seal inserted in the crimp (3*f*) such that no bypass flows can occur outside the nozzle (3) into the powder cavity (1). The length of the nozzle channel and the length (3*l*) of the central cylindrical part of the nozzle channel (3*a*) are important functional parameters of the nozzle (3) as shown in FIG. 1*a* and FIG. 6*a-c*. Like the length (2*l*) of the mouthpiece (2) the length of the nozzle channel (3*a*) was varied from 3 millimeters to 15 millimeters within the scope of measurements with the test device. Here, too, measurements of the fine particle dose (FPD) showed that the fine particle content is increased when the greater lengths are used (particularly 15 millimeters), i.e. the pulmonary delivery of the nebulised particles is improved when longer nozzles (3) are used. This is explained by the longer duration of effect of shear forces on the gas current or the aerosol in the longer nozzle channels (3*a*). The duration of effect as a whole is very short because of the high speed of the gas current. Flow simulations have shown that the speed of the gas current in the nozzle (3) may achieve values of up to Mach 1.

The speed in the nozzle is dependent on the aerodynamic cross-section of the nozzle (3). With a smaller cross-section of the nozzle channel (3*a*) the flow resistance of the nozzle increases and the breaking up of the particles of formulation is increased. This has been demonstrated by the results of measurements (without pulsing of propellant) with different cross-sections of nozzle channels (3*a*). Cross-sections ranging from 0.2 to 0.8 square millimeters were tested (e.g. variation of a circular diameter in the range from 0.5 to 1 millimeter)—cross-sections ranging from 0.4 to 0.7 square millimeters for the nozzle channel (3*a*) are preferred, according to the results of the measurements. For these measurements, the ratio of fine particle dose (FPD) to the total amount of active substance expelled from the nebuliser was evaluated. This ratio increased as the cross-section became smaller. By using smaller diameters for the nozzle channel (3*a*) and hence smaller cross-sectional areas, a higher shear gradient can be obtained. This acts with greater force on the particles that are to be nebulised, so that the fine particle content of the aerosol is increased. By way of example, a measurement of this kind was also carried out with a nozzle channel (3*a*) having an oval rather than a round cross-section. With the same cross-sectional area, in measurements with the oval nozzle channel, an FPD value comparable to that of the round nozzle channel was obtained, and the emptying of the powder cavity was increased when using the oval channel.

Further measurements (without pulsed propellant) with different nozzle channels (3*a*) show a further effect, besides the improved break-up of particles at small cross-sections of the nozzle channels (3*a*). The entire quantity of formulation expelled from the nebuliser shows a particular dependency on the cross-section of the nozzle channel (3*a*). It exhibits the lowest value by comparison (62% in the actual measuring series, based on the quantity of formulation introduced into the powder cavity (1)), at a cross-sectional area of 0.2 square millimeters, while a significantly higher value (73%) is obtained at 0.4 square millimeters, which initially increases slightly at even larger cross-sections (76% at 0.5 square millimeters) and then tends to decrease slightly once more (73% at 0.8 square millimeters). When nozzles (3) with very narrow nozzle channels (3*a*) are used, less powder is expelled from the system, and instead more powder is left behind in the powder cavity (1).

In order, nevertheless, to promote emptying even at small diameters of the nozzle channel (3*a*), an inlet cone (3*b*) is provided in front of the nozzle channel (3*a*) to assist the entry of the powder. As the aerosol reaches a speed in the nozzle channel (3*a*) which is many times higher than the flow rate applied in the mouthpiece (2), there is additionally an outlet cone (3*c*) at the end of the nozzle (3), in order to reduce any turbulence occurring during expulsion. Measurements taken by way of example furthermore indicate that the entire quantity of formulation expelled from the nebuliser is increased by the use of oval cross-sections. However, it was all the more possible to counteract the effect that the emptying from the powder cavity (1) deteriorates on transition to the smaller nozzle channels (3*a*) by pulsing the propellant. Particularly at diameters of the nozzle channel (3*a*) of only 0.5 millimeters, good deliveries were achieved by using pulsed jets of propellant (for example, 92.5% expulsion of 75 milligrams of a powder mixture containing 98% fenoterol from a tub-shaped powder cavity (1), achieving 16.5 milligrams of fenoterol as the actual fine particle content). By dividing a jet of propellant into a number of short bursts or pulses, it is thus possible on the one hand to obtain a high inhalable fine particle content with each pulse (using small cross-sections for the nozzle channel (3*a*)) and also on the other hand to achieve efficient emptying of the powder cavity by the cumulative effect of the pulses. This is certainly the case for powder cavities (1) with a trough-shaped well (1*a*) as shown in FIG. 7*a*, but can also be applied to teardrop-shaped powder cavities (1) as shown in FIG. 7*b*, and to other cavity shapes, particularly if they are designed to hold large amounts of powder in the region of more than 21 milligrams, and the large amount of powder cannot be expelled directly with one jet of propellant through a small-diameter nozzle.

Figure 8A:
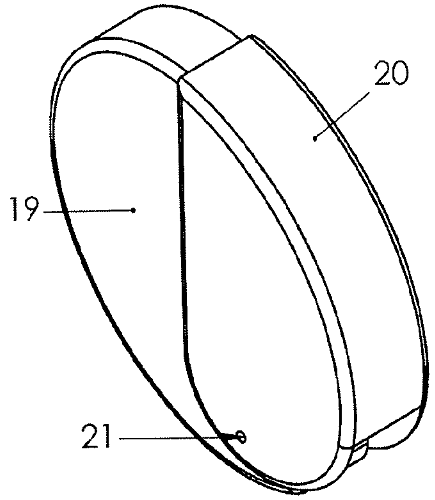
FIG. 8*a* shows the inhaler from outside with the mouthpiece cover closed.
Figure 8C:
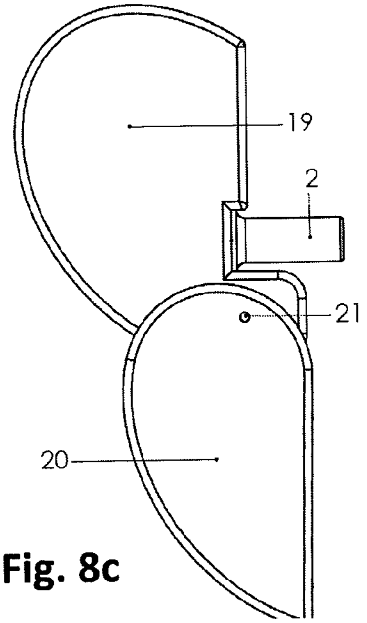
FIG. 8*b* shows it in schematic sectional view and FIG. 8*c* shows it from outside with the mouthpiece opened.
Figure 8B:
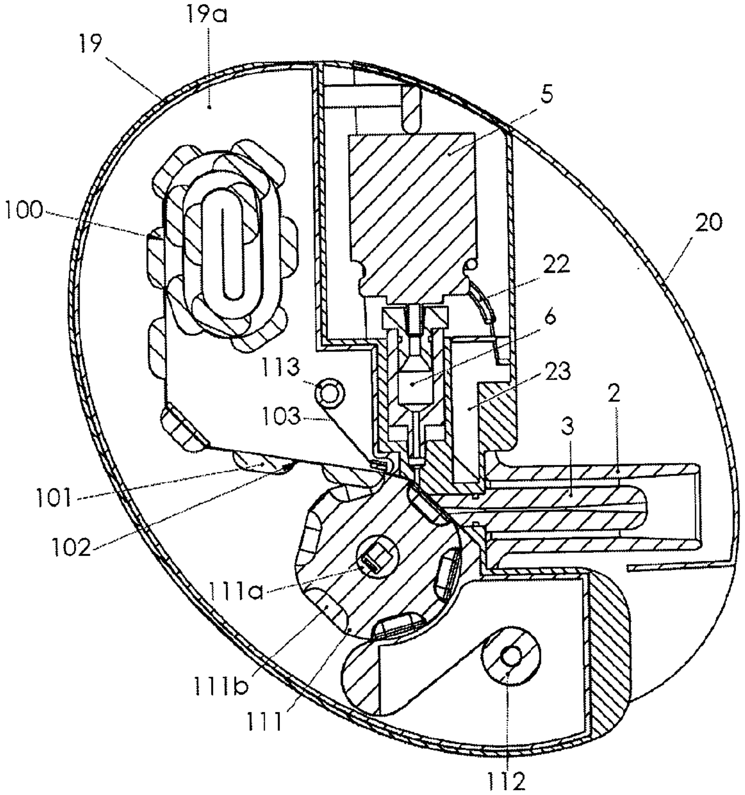

FIG. 8 shows a nebuliser according to the invention which can be used as an inhaler by a patient and is designed as a compact hand-held device. The mode of operation of this inhaler is the same as that described with reference to the test device in FIG. 2. In particular, all the preceding descriptions relating to the mouthpiece (2), the nozzle (3), the cartridge (5) and the vaporiser (6), can also be applied to the inhaler shown in FIG. 8. As can be seen from FIG. 8 these components are arranged analogously to the embodiment in FIG. 2. FIG. 8*a* shows the exterior, with the mouthpiece cover open. The inhaler comprises, as said mouthpiece cover, a cover (20) which is connected to a housing (19) via a rotation spindle (21). When the inhaler is not in use the cover (20) can remain closed and covers the mouthpiece (2) of the inhaler. In this transportable state with the cover (20) closed, only the housing (19) and cover (20) are accessible from outside, and all the components involved in the operation of nebulisation are protected from contamination. The attachment of the cover (19) by means of a rotation spindle (21) of pivotal design in this case allows ease of opening of the inhaler and ensures that the cover (20) remains on the inhaler and cannot become lost. FIG. 8*b* shows a schematic section through the inhaler which in this embodiment is configured as a pmDPI, i.e. as a multi-dose device with individual pre-metered and individually stored dosage units of a powdered formulation. The individual dosage units are preferably arranged on strip-like carriers, particularly a so-called blister strip (100), comprising blister cavities (101) arranged in a line one after another, these blister cavities (101) being formed between a carrier web (102) and a cover film (103). In particular, the carrier web preferably made of a plastics and/or aluminium comprises for this purpose depressions which are produced for example by a thermoforming process. Preferably, the blister cavities (101) comprise tub-shaped or teardrop-shaped wells (1*a*), as described with reference to FIG. 7 *a-c*. The blister cavities (101) are filled with the powdered formulation and can be moved stepwise using a wheel (111) into a position in which they take on the function of the powder cavity (1) in a functional arrangement analogous to the test device in the preceding Figures. The wheel (111) comprises for this purpose well-shaped or pouch-like receptacles (111*b*) distributed equidistantly along its outer periphery, which can accommodate the blister cavities (101) on the side of their carrier web (102) and rotate them into the powder removal position in which they are adjacent to the propellant feed line from the vaporiser (6) and to the nozzle (3). At the powder removal position, the device comprises a seal that prevents the propellant gas from escaping past the blister cavity (101) and exiting again through the nozzle alone. Preferably, before reaching the powder removal position, the cover film (103) is pulled off the carrier web and thus opened. The cover film is preferably wound onto a reel (113). In relation to the advance of the blister strip (100) the cover film (103) is separated from the carrier web (102) at such a late stage that only the blister cavity (101) that has just been brought into the powder removal position is opened, and no other blister cavities (101) which still contain powder are opened. The carrier web (102) with the emptied depressions of the blister cavities (101) is wound onto another reel (112). For this purpose, between the powder removal position and the reel (112), it is preferably passed through a device (not shown in the drawings) in which the carrier web (102) is smoothed out and/or the depressions contained in it are pressed flat. A device of this kind can be found for example in the specification WO2007096111 A2 (page 5 and the remarks relating to FIGS. 2 and 4 therein) and the disclosure to this effect is fully incorporated by reference herein.

At the powder removal position, the opened blister cavity (101) is brought close up to, or pressed against, the connector which comprises the propellant supply line and the inlet of the nozzle channel (3*a*). For example, the wheel (111) and the blister strip (100) are oriented at this point such that the blister cavity (101) is pressed or forced against the connector. The receptacles (111*b*) on the wheel (111) are embodied such that the top of the blister cavity (101) has the same convexity as the associated underside of the connector—preferably, the blister cavity (101) lies completely flat on the wheel (111) and is not domed. Preferably, the connector contains materials which in particular seal the upper outer edge of the opened blister cavity (101) against the connector, such as a Teflon coating or a sealing ring set into the contact surface.

In addition, pressure is preferably applied to the rotation spindle (111*a*) of the wheel (111) by a spring or the like, so that the wheel (111) is pressed towards the connector and in this way the seal is ensured. As an alternative to the wheel (111), a preferably spring-loaded guide rail may be used. By means of tensile force on the reel (112) first of all the blister cavity (101) is brought into its position on the connector and then pressed on by this guide rail. Depending on the configuration of the blister strip (100) the guide rail may have a smooth surface (in which case it is then also suitable for guiding the blister strip as it advances in the device) or a movable pressure plate with a receptacle (this plate does not come into contact with the blister strip (100) as the latter advances).

In one embodiment of the nebuliser according to the invention the mechanism for pulling off the cover film (103) preferably corresponds to the corresponding mechanism which is disclosed in the specification DE4106379A1. The corresponding content is hereby fully incorporated by reference in the present application. A further development of this transporting mechanism can be found in EP1436216B1.

Preferably, the advance of the blister strip (100) is achieved by moving the cover (20), preferably by the opening action. For this purpose the rotation spindle (21) is preferably coupled to the reel (112), so that when the device is opened the blister strip (100) is pulled in the direction of advance and at the same time the wheel (111) rotates. In this coupling, a kind of non-return barrier is provided for example in the form of a friction clutch such that the rotary movement of the spindle (21) is only transmitted to the reel (112) in one direction (preferably the direction of opening). In addition, the rotation spindle (21) and/or the reel (112) is or are optionally coupled via a transmission (not shown in FIG. 8) to the spindle (111*a*) of the wheel (111) and/or of the reel (113) for winding up the cover film (103). There is also the possibility of the rotation spindle (21) acting directly on the spindle (111*a*) of the wheel (111) and the latter is in turn connected to the two reels (112, 113) via a transmission. With regard to the possible construction of such a transmission and the non-return barrier reference is made here to the specification WO2007134792A1 (page 4 lines 30-34, page 6 line 30 to page 7 line 13, page 8 line 7 to 29, page 9 lines 21 to 29 and page 10 line 25 to page 14 line 13). The content of the corresponding lines in that specification are hereby fully incorporated by reference herein, including the features.

The non-return barrier in relation to the transmission of the rotary movement of the rotation spindle (21) and the spindle (111*a*) of the wheel (111) and/or the reels (112, 113) may furthermore be configured similarly to the non-return barrier disclosed in the specification WO07068896. The respective disclosure is hereby fully incorporated by reference herein.

Alternative Electrical Actuation of Advance

As an alternative to pulling off the cover film (103) and using an associated reel (113), before they reach the powder removal position the blister cavities (101) may also be moved past a different kind of opening device at which the cover film (103) is for example pierced or cut open or otherwise opened at the location of the blister cavity (101).

Preferably, the inhaler is configured such that the blister strip (100), the wheel (111) and the reels (112, 113) and any transmission elements acting between them are located in an exchangeable housing part (19*a*). As a result, the size of the inhaler is not determined by the length of the blister strip (100), i.e. it is not determined by the maximum possible number of doses.

In order to expel the powder from the blister cavity (101) which has been brought into the powder removal position, propellant is released from the cartridge (5). This can either be achieved by the user or patient pressing directly on the cartridge (5) in the direction of its valve stem (7), which in this case is preferably spring-loaded, (application of pressure to the cartridge base on the opposite side from the valve stem (7)) or by the patient triggering a corresponding movement of the cartridge (5) and/or the pulse sequence on a built-in magnetic valve by breathing in through the mouthpiece (2).

A so-called breath actuation of this kind is provided in the device shown in FIG. 5*a*.

FIG. 5 shows a tiltable lug (22) which keeps the cartridge (5) in a resting position slightly spaced from the valve stem receptacle (8*a*), so that the valve of the cartridge (5) is closed. If the patient then breathes in through the mouthpiece (2), he generates suction, particularly at the inlet opening (2*b*) of the mouthpiece, which also extends to the adjoining cavity, which in the embodiment shown constitutes a bypass (23) in which air can flow past the vaporiser. The inlet opening of this bypass connected to the atmosphere is closed off by part of the lug in the resting position. As a result of the suction produced during the breathing-in process the lug (22) tilts so that at one end the inlet opening at the bypass (23) is opened up. This clears any blockage of the cartridge (5) and the path of movement for the cartridge (5) at the other end of the lug (22) is opened up downwards or in the direction of the valve stem receptacle (8*a*). Preferably, the cartridge (5) is spring-loaded such that even when the lug (22) is deflected during the breathing-in process it moves in the direction of the valve stem receptacle (8*a*). If the suction produced by breathing in through the mouthpiece (2) decreases in the bypass (23), the lug (22) returns to its original position and the cartridge (5) is again spaced from the valve stem receptacle (8*a*). Depending on the strength of the breath actuation, the lug (22) may also be connected to a restoring mechanism for this purpose. After the breath actuation of the movement of the cartridge (5) the cartridge is moved back into the biased starting position, preferably as the cover (20) is closed or opened—preferably by means of a guide bar.

Such a combination of the biasing of a propellant cartridge and a breath actuation is disclosed in U.S. Pat. No. 5,031,610. The corresponding content is hereby fully incorporated by reference in the present application. In U.S. Pat. No. 5,031,610 the biasing of the cartridge and the provision of the breath actuation is brought about by the removal and replacement of a cap on the mouthpiece. In an embodiment that is preferred here the mechanism from U.S. Pat. No. 5,031,610 would instead be coupled to the pivoting movement of the cover (20) or to an additional lever (not shown).

As an alternative to a mechanical breath actuation of this kind, an electromechanical control may also be used. In embodiments of this kind with electromagnetic control (not shown) the nebuliser preferably has a battery which provides the electric voltage needed for such controls. In electrical or electromechanical breath actuation of this kind, the nebuliser comprises on the inside of the mouthpiece (2) an electrical flow sensor which emits an electrical signal that varies with the flow rate, in accordance with the flow detected. This signal is then used to start an electromechanical process by which, for example, the cartridge (5) is moved in the direction of the valve stem receptacle (8*a*), the valve of the cartridge (5) is opened and in this way propellant is released into the vaporiser (6) or the channels of the nebuliser. In order that this valve actuation only takes place at a predefined air flow, i.e. a specific suction on the mouthpiece (2), the sensor signal is first passed through a monitoring device, for example an analogue comparator circuit or digital electronics. The sensor signal to some extent triggers an electric switch when a specific suction is obtained at the mouthpiece (2). When this electric switch is actuated an electromechanical process is started, for example a stepping motor is started up which moves the cartridge along. Electromechanical breath-actuated triggering of nebulisers with propellant cartridges is disclosed in the specification WO9207599A1. The corresponding content relating to such actuation is hereby fully incorporated by reference in the present application.

One possible way of introducing breath actuation into the nebuliser, which is independent of the movement of the cartridge, consists in providing a second valve in addition to the valve belonging to the cartridge (5) (preferably where there is no intention of using a magnetic valve actuated by an electronic pulse generator as in FIG. 4). In such an embodiment, the second valve is located before the inlet of the vaporiser (6), from a fluidic point of view. The nebuliser is prepared for the inhalation by actuating the $1^{st}$ valve—e.g. by displacing the cartridge (5), the displacement being coupled to the opening of the cover (20)—and the propellant released flows into an antechamber in front of the second valve. Then, to trigger the breath actuation, the $2^{nd}$ valve is simply opened, which requires the application of less force than the displacement of the cartridge (5) needed to actuate the first valve. An embodiment of this kind with a second valve in addition to the metering valve of a cartridge (5) may comprise a valve arrangement and its coupling to a breath-actuated means as disclosed in the specification GB2233236A, which is directed to the breath-actuated triggering of an MDI. The corresponding content relating to such arrangements is hereby fully incorporated by reference in the present application. The second valve is opened directly by the suction applied by the patient, e.g. by the application of suction to a plate or die connected to the opening of the second valve or by the indirect application of suction to a component which belongs to a second valve otherwise closed by magnetic forces. A plate or die of this kind is provided in the embodiment of the nebuliser under consideration here, preferably in the bypass (23). Preferably, the second valve is additionally designed, e.g. by means of a resilient limit stop when deflected and/or by means of additional biasing, such that when breath-activated it opens in pulsed manner, i.e. after opening it springs back into the closed position, as the breathing is maintained it opens again, closes again and so on.

Preferably, the nebulisers described here are operated with a medicinal formulation which comprises a constituent from the disclosure of the European Patent Application with the application Ser. No. 12/151,105.9 on page 26 line 12 to page 63 line 2 or corresponds to one of the formulations mentioned therein. The content of these lines is hereby fully incorporated by reference, including the features, in the present application.

LIST OF REFERENCE NUMERALS

1 powder cavity
1*a* well (in powder cavity)
1*b* sealing groove
1*c* slope (in powder cavity)
1*d* flattened area (in powder cavity)
1*t* carrier (of powder cavity)
2 mouthpiece
2*a* passage (at the mouthpiece)
2*b* inlet opening (at the mouthpiece)
2*l* length (of the mouthpiece)
3 nozzle
3*a* nozzle channel
3*b* inlet cone (of the nozzle)
3*c* outlet cone (of the nozzle)
3*d* end face (of the nozzle)
3*g* connecting end (of the nozzle)
3*f* crimp
3*l* length (of the cylindrical part of the nozzle channel)
4 connector
5 cartridge
6 vaporiser
7 valve stem
8 cover (on the vaporiser)
8*a* valve stem receptacle (in the cover)
8*b* flange (on the cover)
8*c* crimp (in the flange)
8*d* inner cone (on the cover)
9 body (of the vaporiser)
9*a* cavity (of the vaporiser)
9*b* funnel
9*c* outlet (of the vaporiser)
9*d* stem (on the vaporiser)
10 seal
11 bead
12 wire
13 magnetic valve
14 flange plate
15 microfluidic oscillator
15*a* inlet channel (at the microfluidic oscillator)
15*b* partial channels
15*c* internal walls (of the partial channels)
15*d* mixing region
15*e* projections in the mixing region
15*f* outlet (from mixing region of the microfluidic oscillator)
15*t* flow distributor
15*v* ventilation channel
19 housing
19*a* replaceable housing part
20 cover (for mouthpiece)
21 rotation spindle (for cover)
22 lug
23 bypass
100 blister strip
101 blister cavity
102 carrier web
103 cover film
111 wheel
111*a* rotation spindle (on wheel)
111*b* receptacle (on wheel)
112 reel (for carrier web)
113 reel (for cover film)
α inlet angle (on nozzle)
β outlet angle (on nozzle)
A aerosol
G pulse generator
I nebuliser
K propellant gas cartridge
Q source (gas)
R(p) pressure regulator
R(F) flow regulator
V magnetic valve
WT heat exchanger

The invention claimed is:

1. An apparatus for nebulising powdered medicinal formulation, wherein the nebulisation is assisted by a propellant which is supplied to a cavity in which is contained a measured amount of the powdered medicinal formulation, characterised in that the apparatus comprises a device which has an inlet at which propellant is present, and through which the propellant can be conveyed, said device causing such flow characteristics in the propellant as it passes through that it exits the device in the form of a plurality of successive pulses or bursts which are kept distinct from one another and is supplied to the cavity in the form of a plurality of successive pulses or bursts which are kept distinct from one another; and a dosing valve producing a single dose of the propellant upstream of the device and delivering the single dose of the propellant to the device such that the single dose of the propellant is converted into the plurality of successive pulses or bursts of propellant, which ejects a single dose of the powdered medicinal formulation from the apparatus to the patient within a time interval which corresponds to a time a patient draws breath, wherein during the operation of the apparatus the device produces relatively low duty cycle pulses in which each pulse has a relatively short on-time where the pressure is relatively high followed by a relatively long off-time where the pressure is permitted to fall to or near zero.

2. The apparatus according to claim 1, characterised in that the pulses or bursts are kept distinct from one another such that the flow of propellant comes to a standstill between the pulses and/or the pressure of the propellant leaving the device falls to zero or virtually zero.

3. The apparatus according to claim 1, characterised in that the propellant is stored in the form of liquefied propellant gas in a container or a cartridge (5), the apparatus having a metering valve for removing a measured volume of propellant from the container or the cartridge (5) and the device being located downstream of the metering valve.

4. The apparatus according to claim 3, characterised in that the device generates the pulses in the propellant such that the measured volume of propellant is divided into pulses or bursts in such a way that the division of the measured volume into pulses or bursts corresponds to a distribution of 100 microliters between at least 7 pulses or bursts.

5. The apparatus according to claim 1, characterised in that the propellant is supplied through a valve which divides the propellant present into a plurality of pulses by means of a plurality of opening and closing processes.

6. The apparatus according to claim 5, characterised in that the valve is an actuatable magnetic valve (13).

7. The apparatus according to claim 5, characterised in that during the operation of the apparatus the valve has opening times in the range from 3 to 30 milliseconds, and closure times in the range from 60 to 500 milliseconds.

8. The apparatus according to claim 1, characterised in that the propellant is supplied through a channel structure forming a microfluidic oscillator in which the pulses or bursts are produced in the propellant.

9. The apparatus according to claim 8, characterised in that the channel structure comprises at least one fork and a mixing region for fluid jets.

10. The apparatus according to claim 1, characterised in that before being fed into the cavity the propellant is passed through a vaporiser (6) or heat exchanger.

11. The apparatus according to claim 10, characterised in that the vaporiser (6) has a cavity (9*a*) and contains in its cavity (9*a*) one or more heat exchange elements.

12. The apparatus according to claim 11, characterised in that metal beads and/or metal wires form the heat exchange element or the heat exchange elements.

13. The apparatus according to claim 1, characterised in that a propellant stream charged with powdered medicinal formulation is conveyed from the cavity into a nozzle (3) and the nozzle (3) comprises a substantially rectilinear nozzle channel (3*a*).

14. The apparatus according to claim 13, characterised in that the feed line for propellant into the cavity and the axis through the nozzle channel (3*a*) both meet at an angle of between 30° and 45° in the cavity and/or at this angle relative to the base of the cavity.

15. The apparatus according to claim 13, characterised in that the nozzle channel (3*a*) comprises an inlet cone (3*b*) and/or an outlet cone (3*c*) and/or a wall of the nozzle channel (3*a*) is cylindrical, at least in a central region.

16. The apparatus according to claim 13, characterised in that the cavity in which a measured amount of the powdered medicinal formulation is contained in a powder cavity (1) which is streamlined in shape.

17. The apparatus according to claim 16, characterised in that the powder cavity (1) has a teardrop shape, a narrower end of the teardrop shape pointing in a direction of an inlet of the nozzle channel (3*a*).

18. The apparatus according to claim 16, characterised in that the powder cavity (1) has a powder cavity well (1*a*), which has a slope (1*c*) on a bottom of the powder cavity well (1*a*), this slope (1*c*) conveying the flow in the direction of the inlet of the nozzle channel (3*a*).

19. A method for nebulising powdered medicinal formulations, comprising:

supplying a propellant in the form of a plurality of successive pulses or bursts distinct from one another, to a cavity in which there is a measured amount of the powdered medicinal formulation, wherein the propellant is supplied through a channel structure forming a microfluidic oscillator in which the pulses or bursts are produced in the propellant.

20. An apparatus for nebulising powdered medicinal formulation, wherein the nebulisation is assisted by a propellant which is supplied to a cavity in which is contained a measured amount of the powdered medicinal formulation, wherein the apparatus comprises a device which has an inlet at which propellant is present, and through which the propellant can be conveyed, said device causing such flow characteristics in the propellant as it passes through that it exits the device in the form of a plurality of successive pulses or bursts which are kept distinct from one another and is supplied to the cavity in the form of a plurality of successive pulses or bursts which are kept distinct from one another, and the propellant is supplied through a channel structure forming a microfluidic oscillator in which the pulses or bursts are produced in the propellant.

21. An apparatus for nebulising powdered medicinal formulation, wherein the nebulisation is assisted by a propellant which is supplied to a cavity in which is contained a measured amount of the powdered medicinal formulation, wherein the apparatus comprises a device which has an inlet at which propellant is present, and through which the propellant can be conveyed, said device causing such flow characteristics in the propellant as it passes through that it exits the device in the form of a plurality of successive pulses or bursts which are kept distinct from one another and is supplied to the cavity in the form of a plurality of successive pulses or bursts which are kept distinct from one another, and wherein during the operation of the apparatus the device produces relatively low duty cycle pulses in which each pulse has a relatively short on-time where the pressure is relatively high followed by a relatively long off-time where the pressure is permitted to fall to or near zero.

22. The apparatus of claim 21, wherein the on-time is in the range from 3 to 30 milliseconds, and the off-time is in the range from 60 to 500 milliseconds.

23. An apparatus for nebulising powdered medicinal formulation, wherein the nebulisation is assisted by a propellant which is supplied to a cavity in which is contained a measured amount of the powdered medicinal formulation, wherein the apparatus comprises a device which has an inlet at which propellant is present, and through which the propellant can be conveyed, said device causing such flow characteristics in the propellant as it passes through that it exits the device in the form of a plurality of successive pulses or bursts which are kept distinct from one another and is supplied to the cavity in the form of a plurality of successive pulses or bursts which are kept distinct from one another, wherein a propellant stream charged with powdered medicinal formulation is conveyed from the cavity into a nozzle (3) and the nozzle (3) comprises a substantially rectilinear nozzle channel (3*a*), and wherein the feed line for propellant into the cavity and the axis through the nozzle channel (3*a*) both meet at an angle of between 30° and 45° in the cavity and/or at this angle relative to the base of the cavity.

* * * * *